(12) United States Patent
Nakagawa et al.

(10) Patent No.: US 11,883,139 B2
(45) Date of Patent: Jan. 30, 2024

(54) SENSOR MODULE AND BLOOD PRESSURE MEASUREMENT DEVICE

(71) Applicant: OMRON HEALTHCARE Co., Ltd., Kyoto (JP)

(72) Inventors: Yuki Nakagawa, Kyoto (JP); Tsuyoshi Kitagawa, Kyoto (JP); Jumpei Mano, Kyoto (JP); Takanobu Yamauchi, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 687 days.

(21) Appl. No.: 17/098,860

(22) Filed: Nov. 16, 2020

(65) Prior Publication Data

US 2021/0059537 A1  Mar. 4, 2021

Related U.S. Application Data

(63) Continuation of application No. PCT/JP2019/020046, filed on May 21, 2019.

(30) Foreign Application Priority Data

May 24, 2018 (JP) .................................. 2018-099726

(51) Int. Cl.
*A61B 5/022* (2006.01)
*A61B 5/00* (2006.01)

(52) U.S. Cl.
CPC ............ *A61B 5/022* (2013.01); *A61B 5/6824* (2013.01); *A61B 2562/0247* (2013.01); *A61B 2562/04* (2013.01)

(58) Field of Classification Search
CPC .................. A61B 5/022; A61B 5/6824; A61B 2562/0247; A61B 2562/04; A61B 5/02141
See application file for complete search history.

(56) References Cited

U.S. PATENT DOCUMENTS

| 6,491,647 B1 * | 12/2002 | Bridger | G01L 1/2231 128/900 |
| 2010/0210956 A1 * | 8/2010 | Im | A61B 5/022 600/490 |
| 2016/0287102 A1 * | 10/2016 | Saponas | A61B 5/02108 |

FOREIGN PATENT DOCUMENTS

| JP | 62-161344 A | 7/1987 |
| JP | 63-100343 A | 5/1988 |

(Continued)

OTHER PUBLICATIONS

International Preliminary Report on Patentability dated Nov. 26, 2020 in International (PCT) Application No. PCT/JP2019/020046.

*Primary Examiner* — Andrey Shostak
(74) *Attorney, Agent, or Firm* — WENDEROTH, LIND & PONACK, L.L.P.

(57) ABSTRACT

The present invention can provide a sensor module and a blood pressure measurement device that improves the protection strength of and prevents damage to a surface that comes into contact with a living body. A sensor module 63 of a blood pressure measurement device 1 includes: a sensor base 72; a pressure sensor portion 71 fixed to the sensor base 72; a sensor head cover 73 fixed to the sensor base 72, the sensor head cover 73 forming a gap portion 79 between an inner surface 73g and the sensor base 72 and the pressure sensor portion 71 and including a rubber portion 75 that forms, on an outer surface, at least a region that comes into contact with a living body and that allows pressure from a wrist 100 to transfer to the pressure sensor portion 71 side; and a soft portion 74 disposed in the gap portion 79 at least between the rubber portion 75 and the pressure sensor portion 71, the soft portion 74 having a lower hardness than the rubber portion 75 and allowing pressure from the rubber portion 75 to transfer to the pressure sensor portion 71.

10 Claims, 34 Drawing Sheets

(56) References Cited

FOREIGN PATENT DOCUMENTS

| | | |
|---|---|---|
| JP | H01-288228 A | 11/1989 |
| JP | 2008-61832 A | 3/2008 |
| JP | 2016-212015 A | 12/2016 |
| KR | 10-2006-0116635 A | 11/2006 |

\* cited by examiner

[FIG. 1]
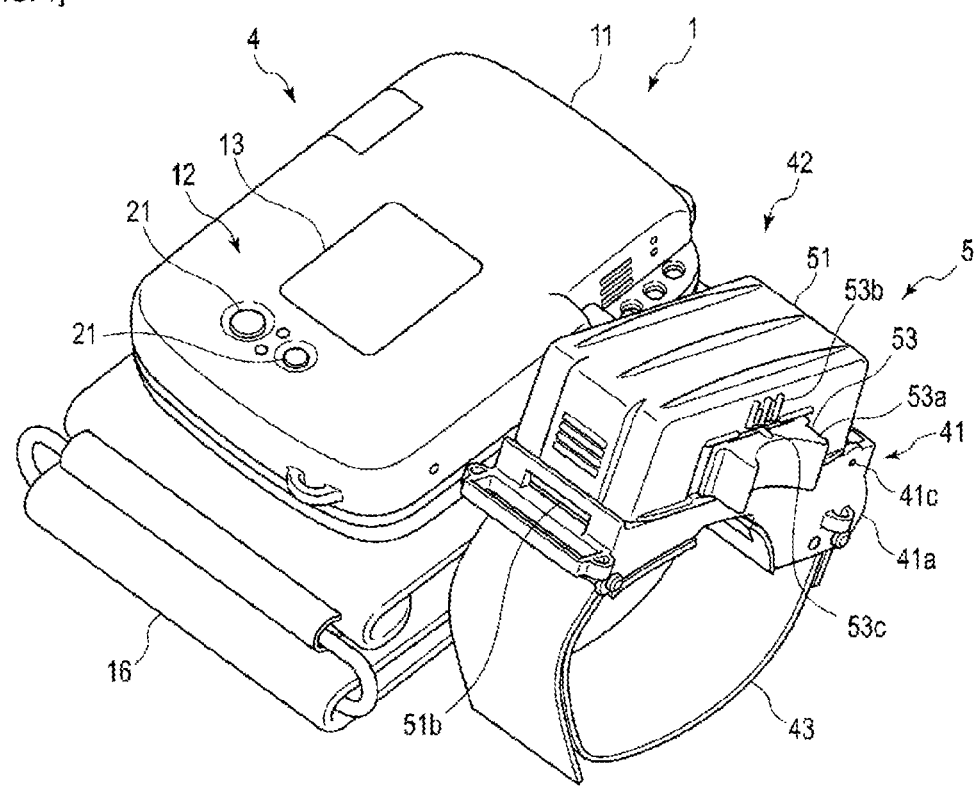

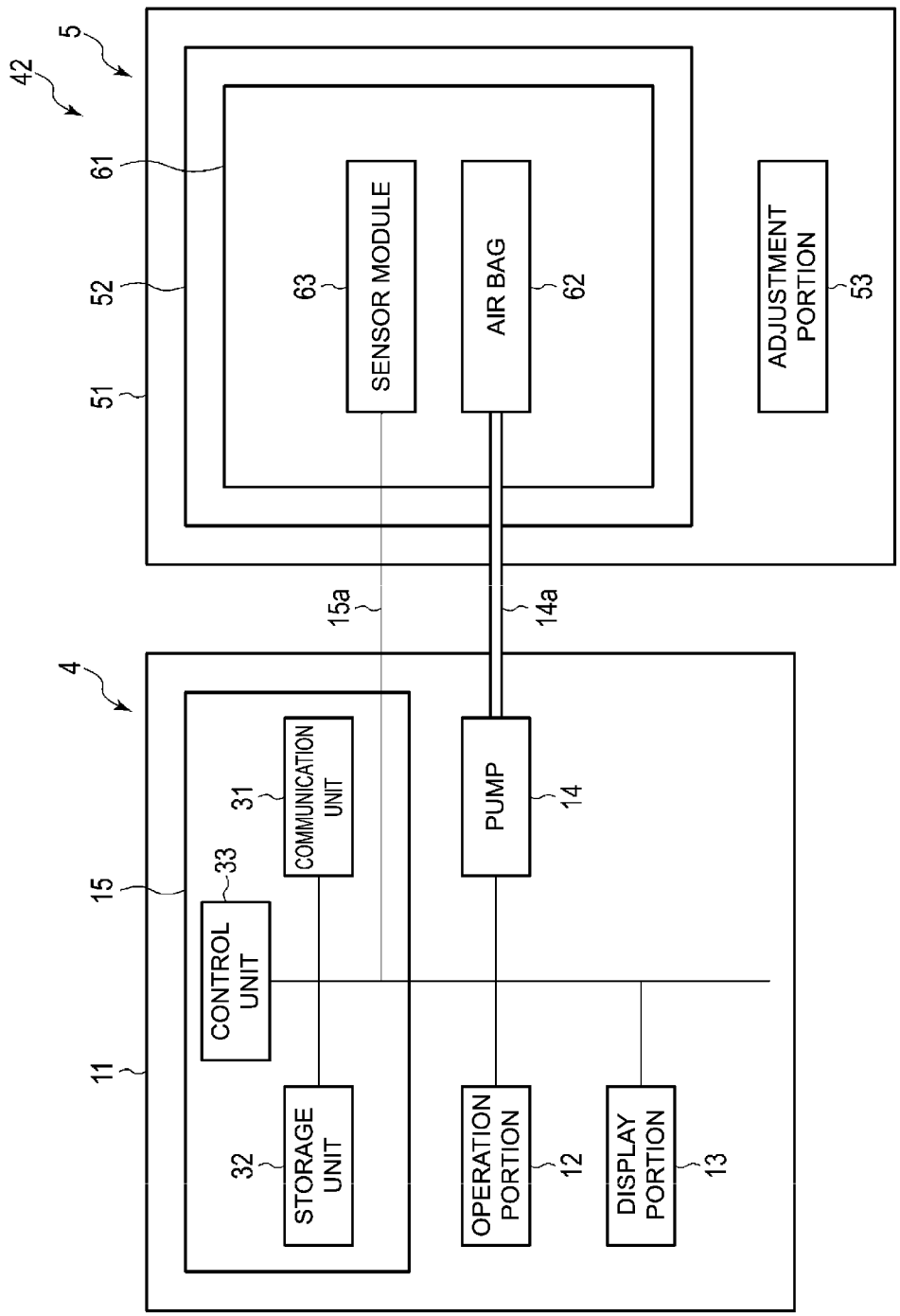
[FIG. 2]

[FIG. 3]
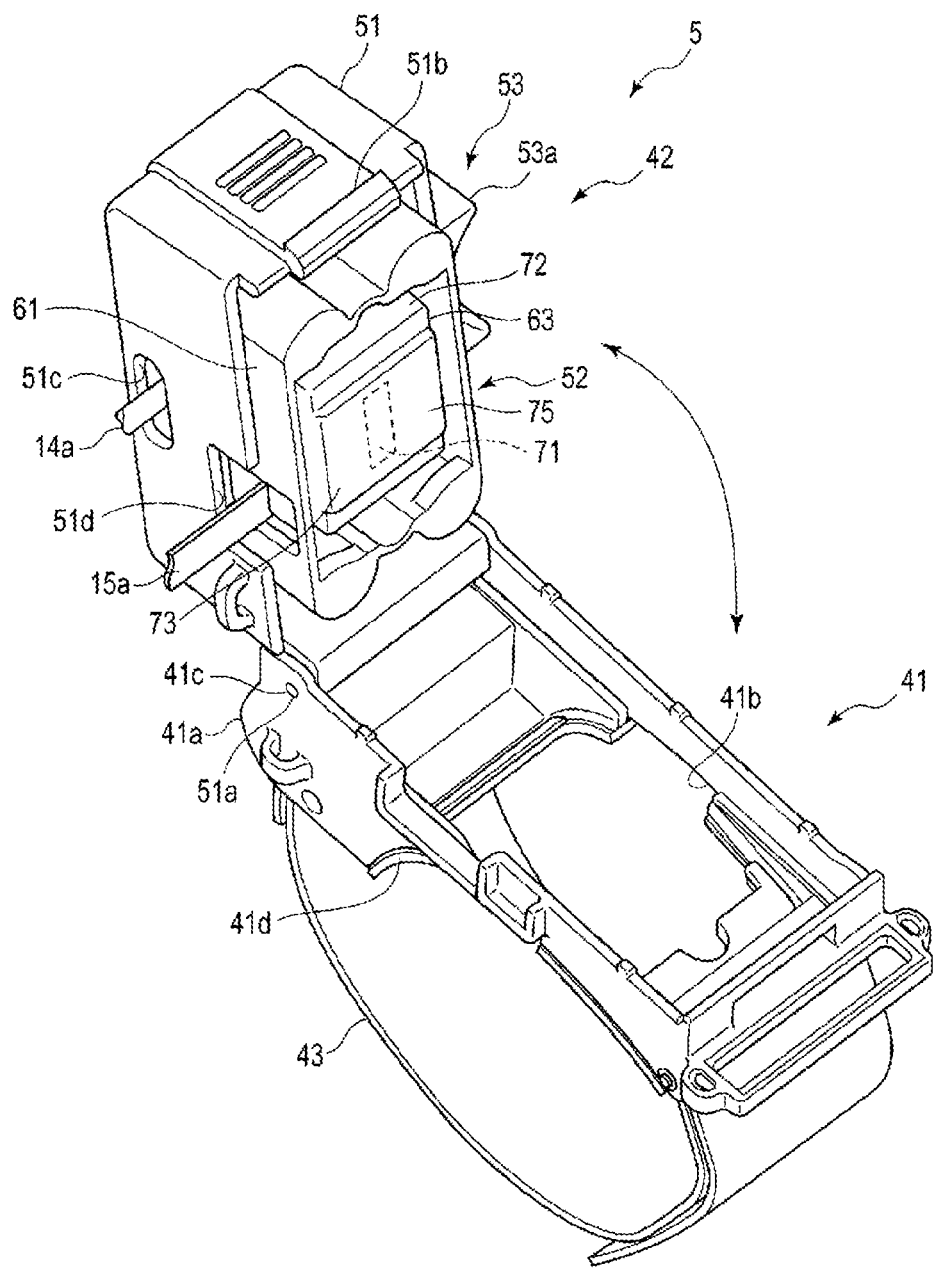

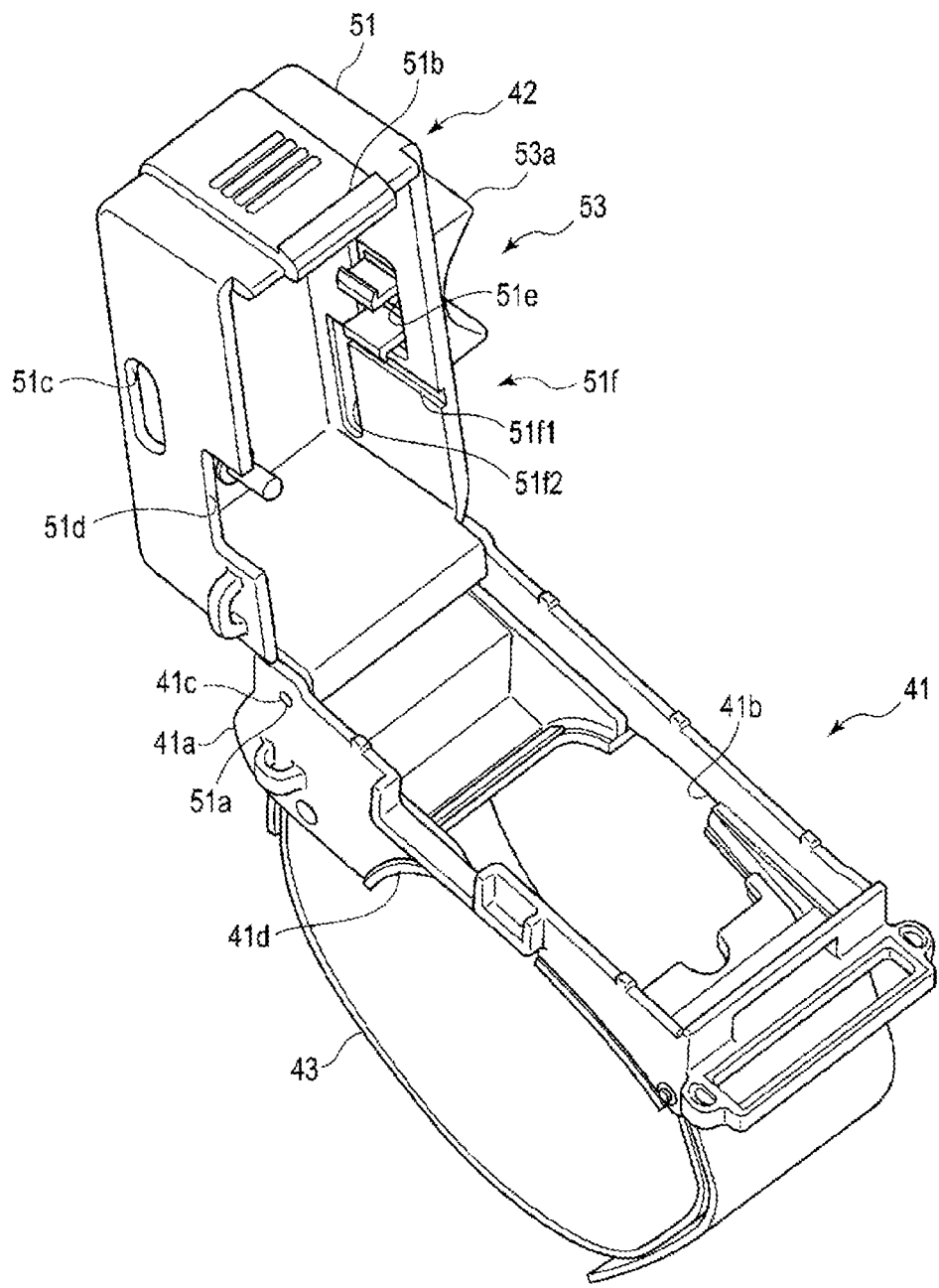
[FIG. 4]

[FIG. 5]
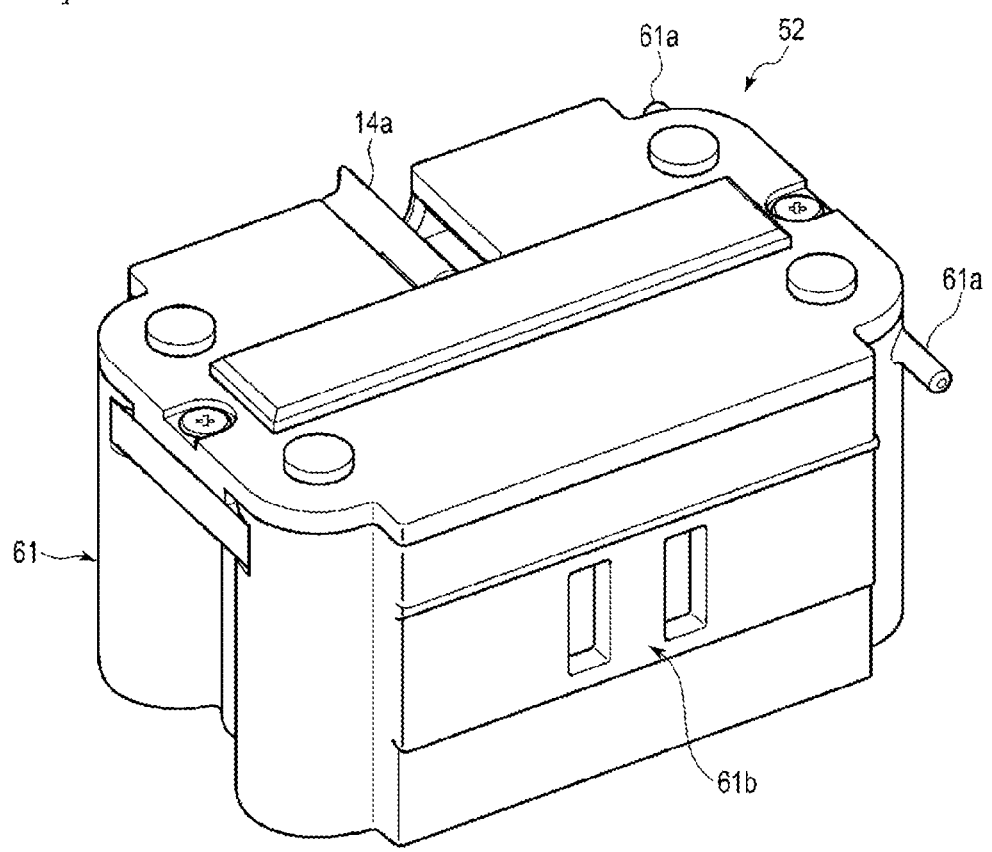

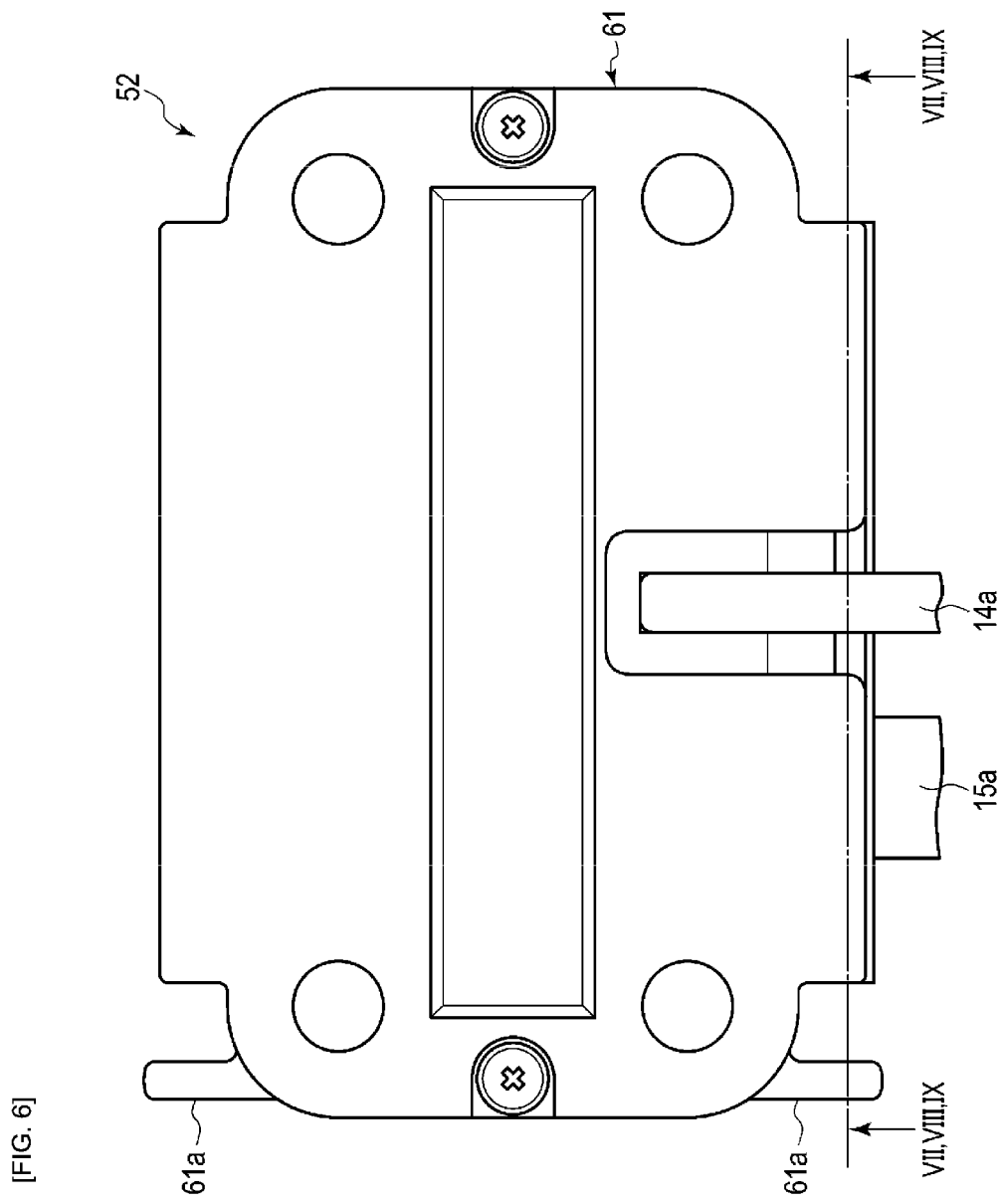
[FIG. 6]

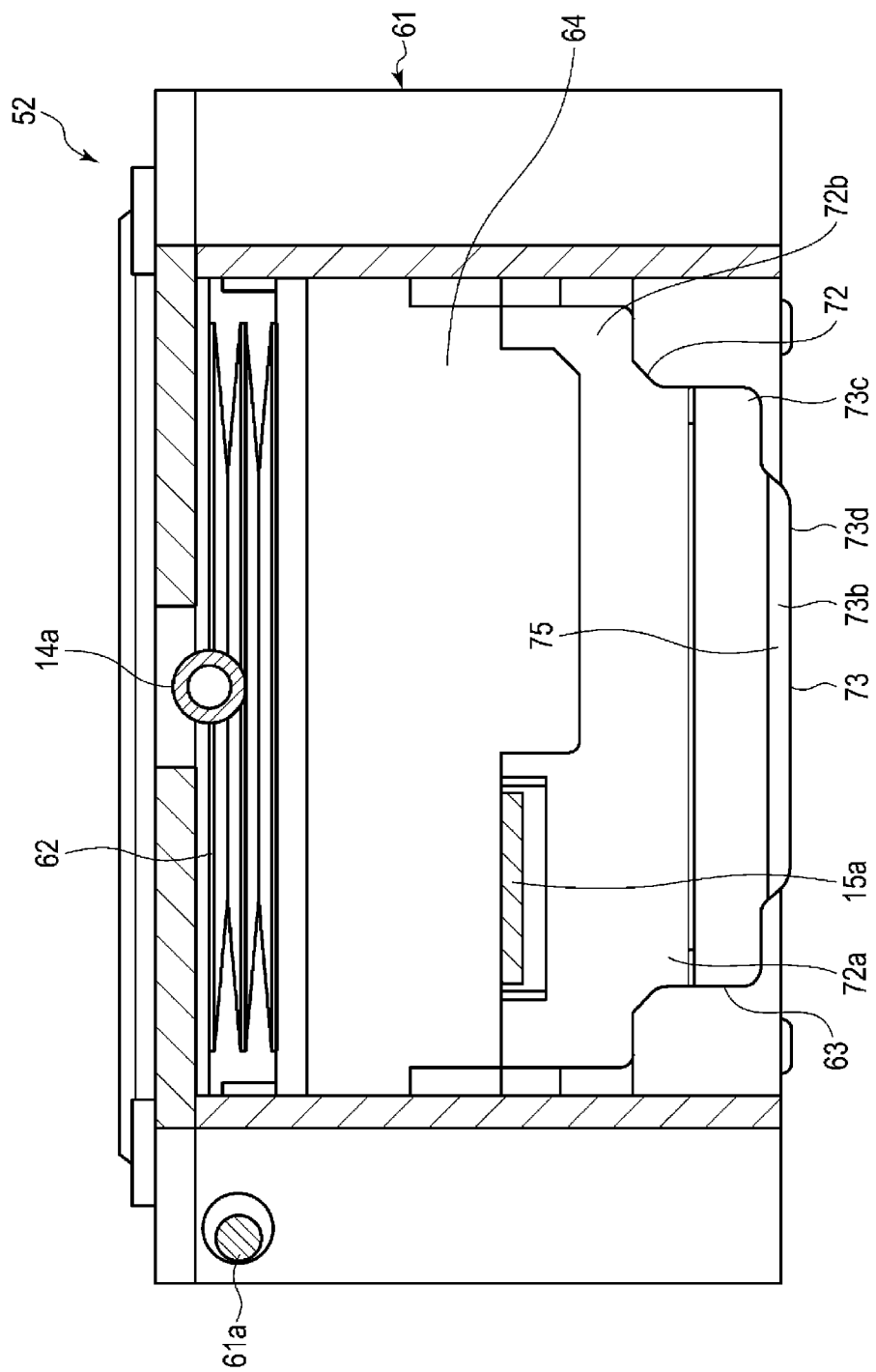

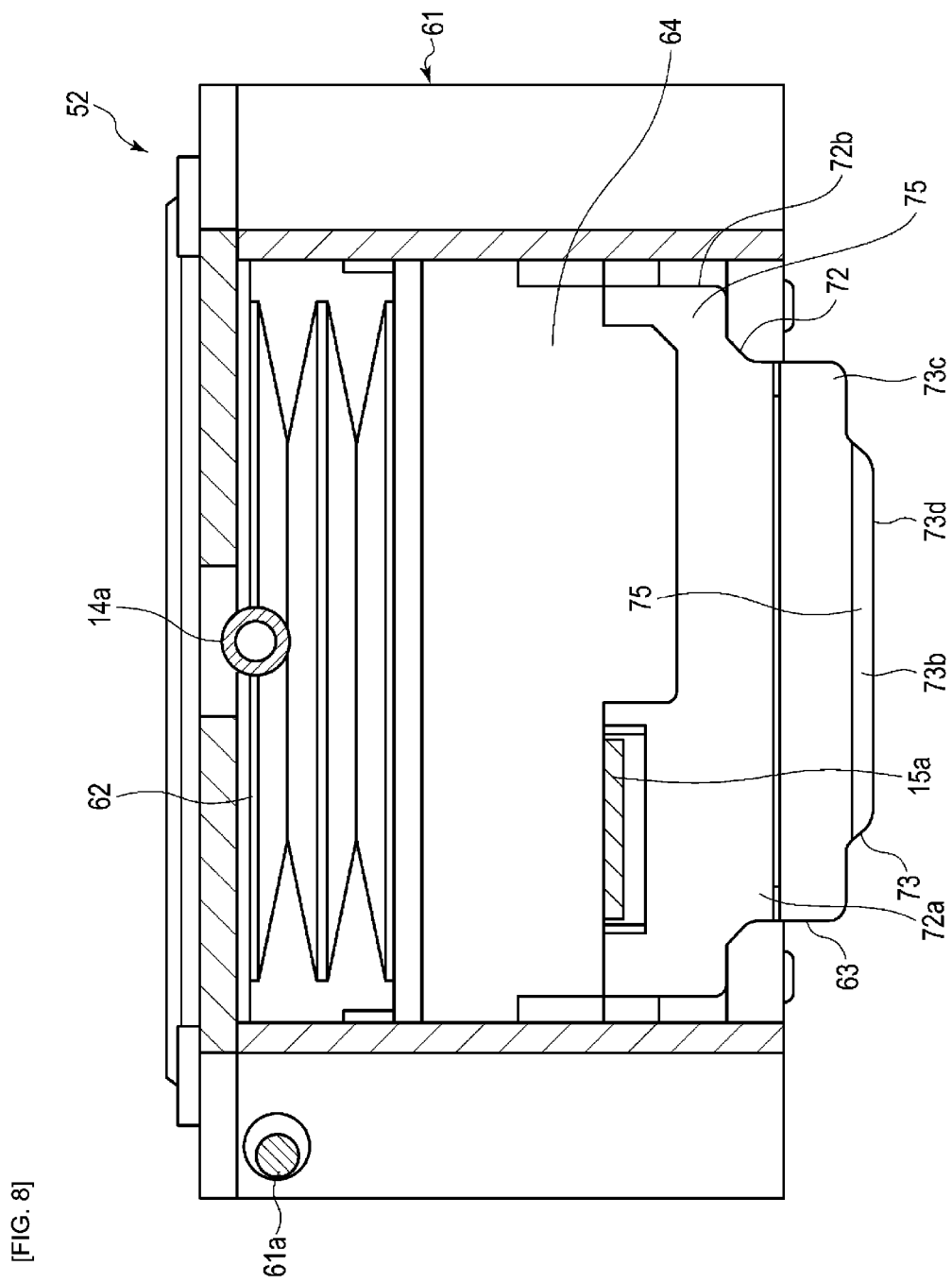

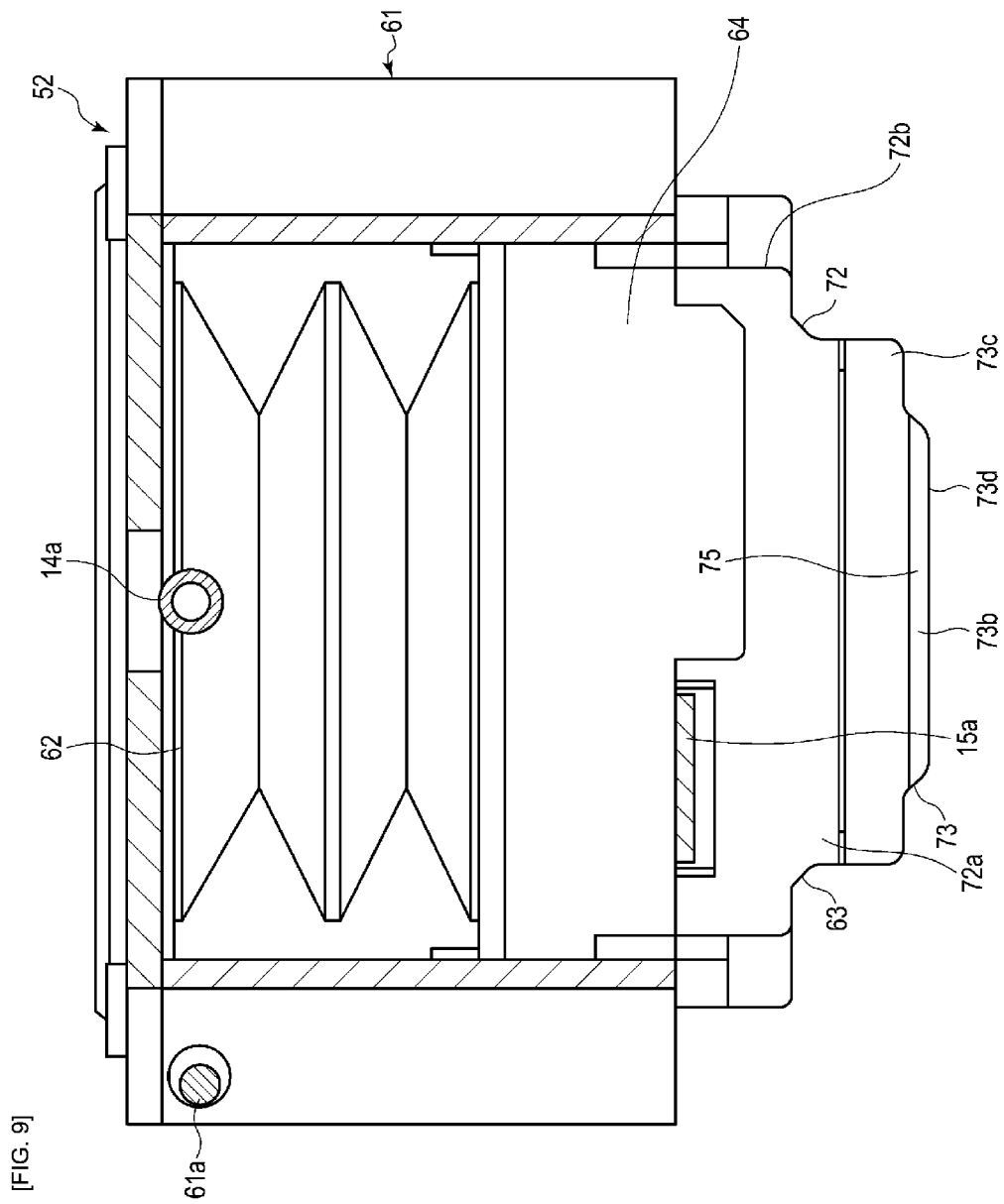
[FIG. 9]

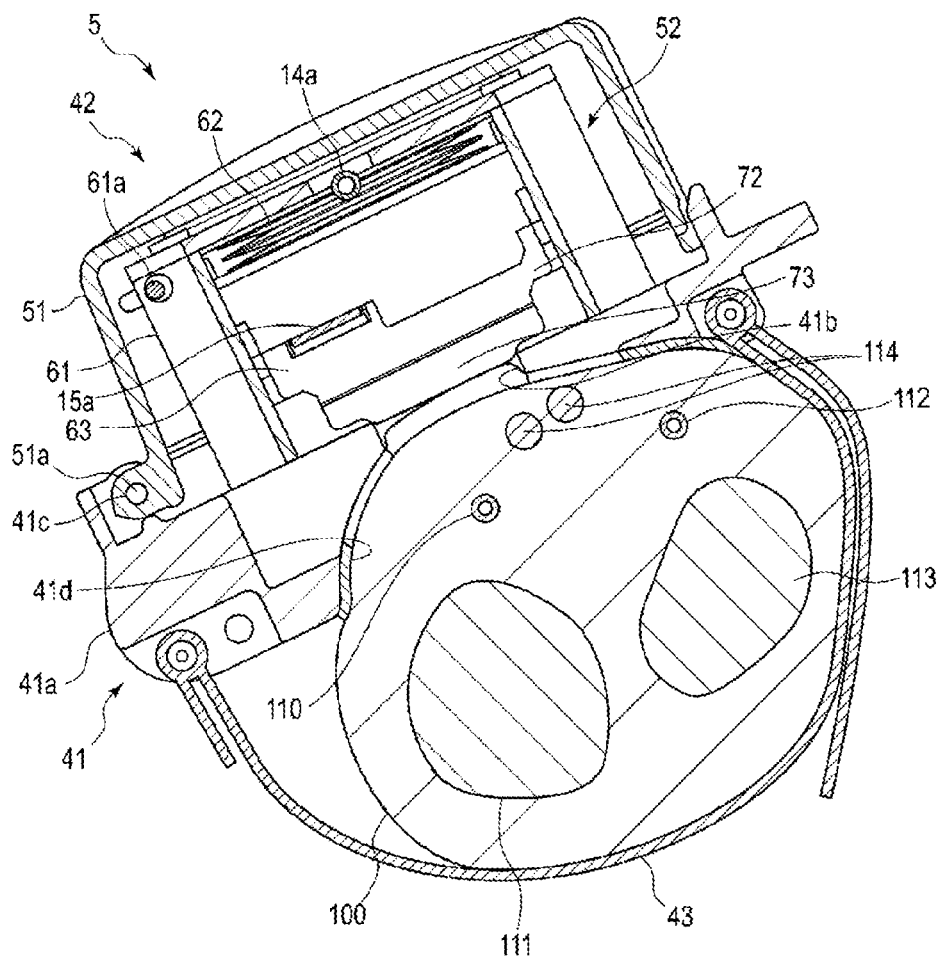
[FIG. 10]

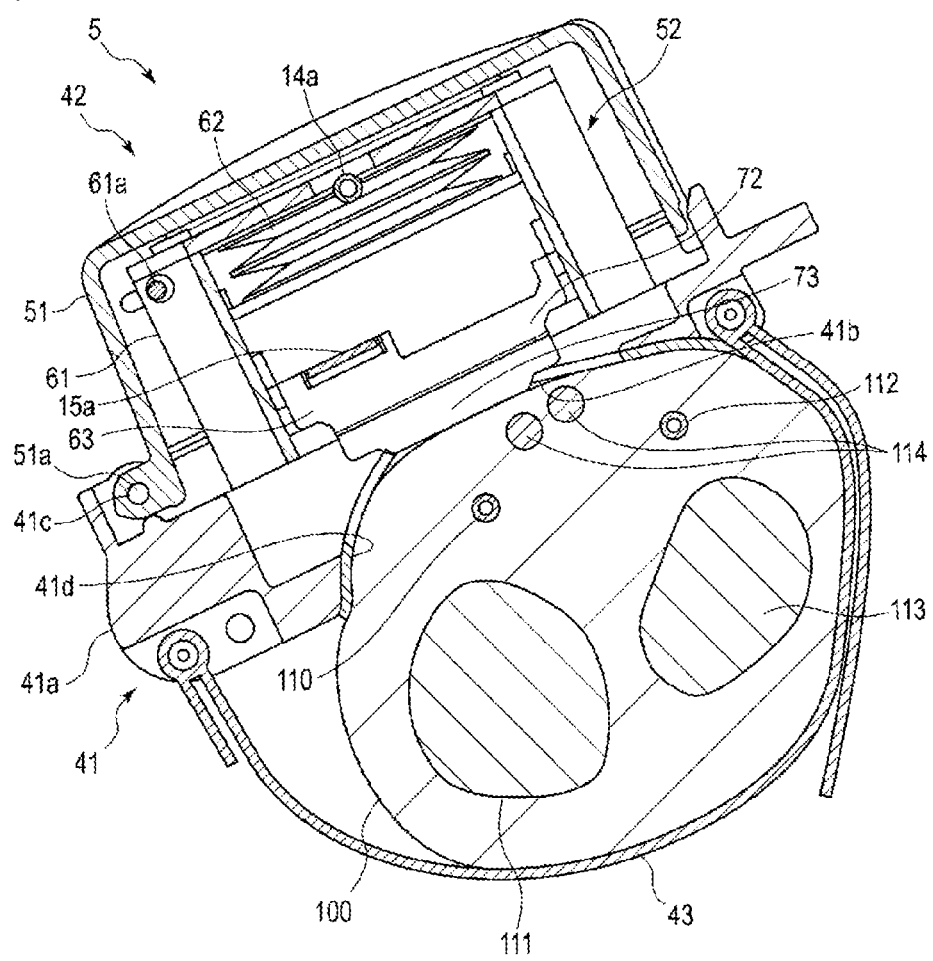
[FIG. 11]

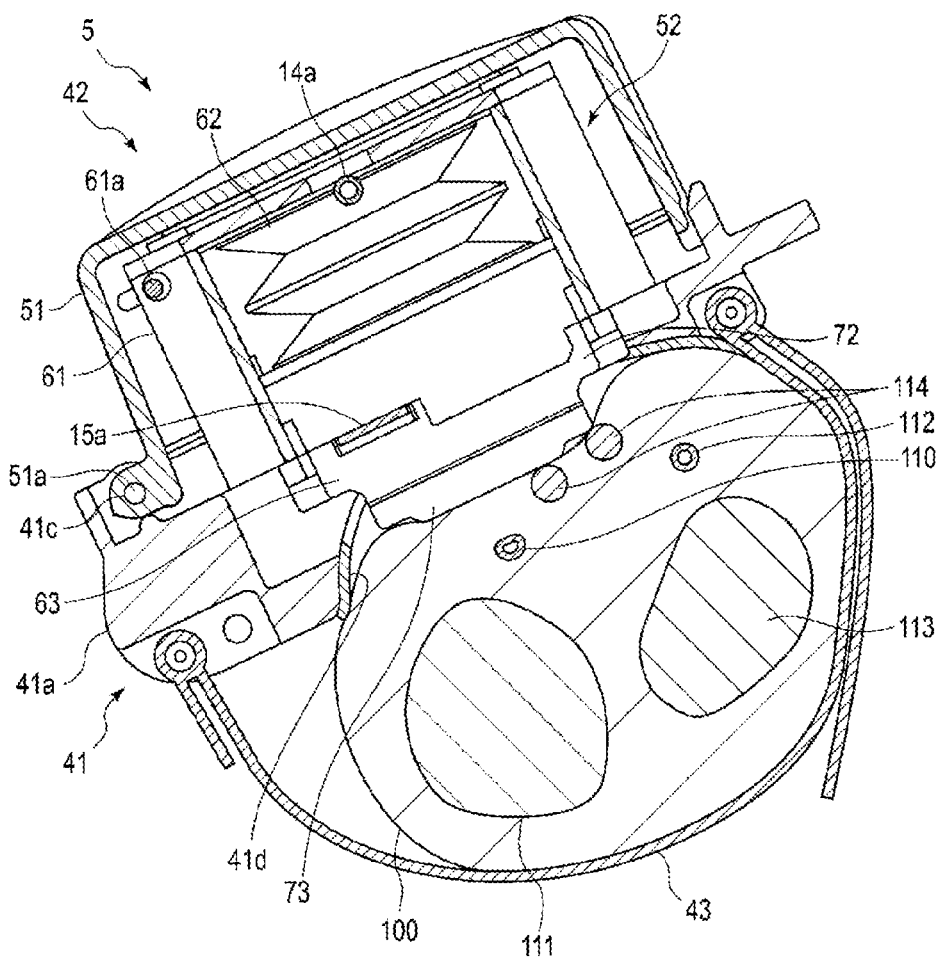
[FIG. 12]

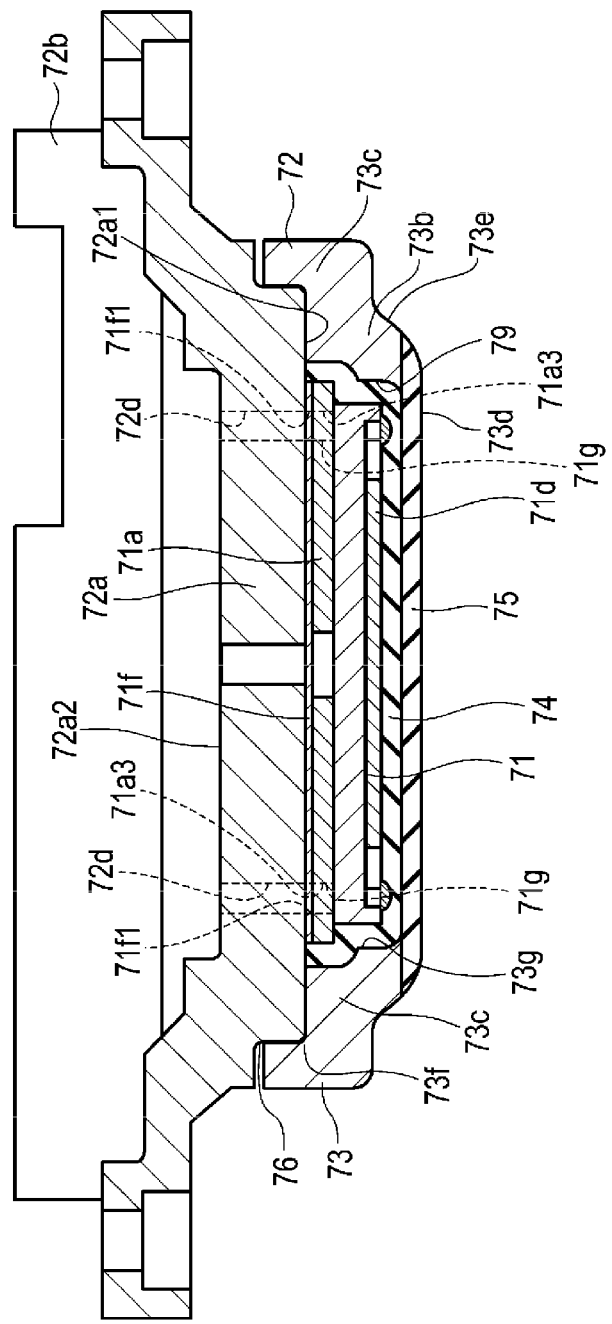
[FIG. 13]

[FIG. 14]
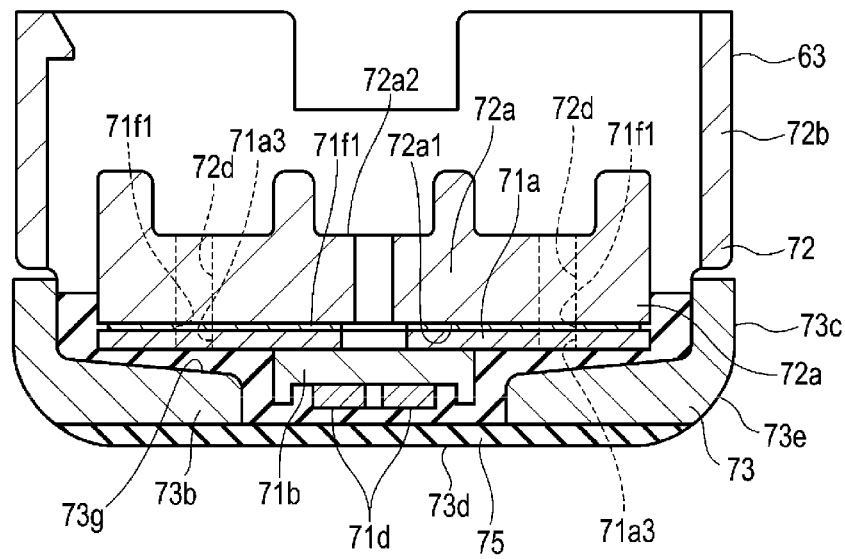

[FIG. 15]
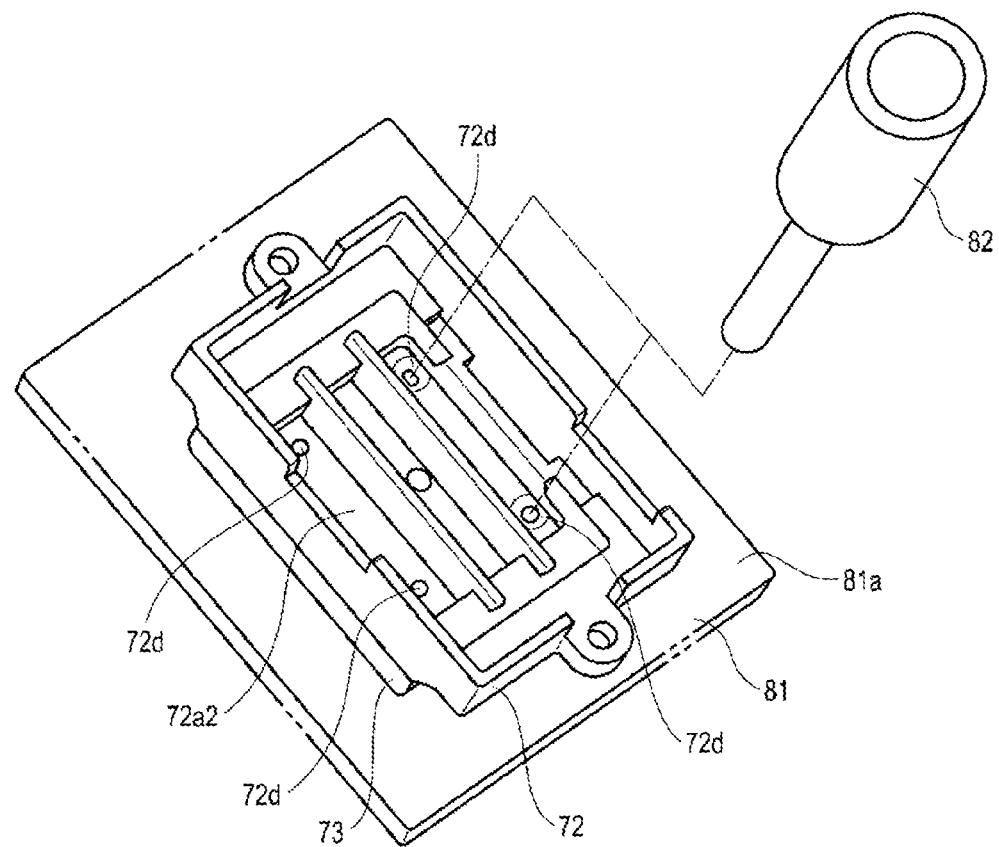

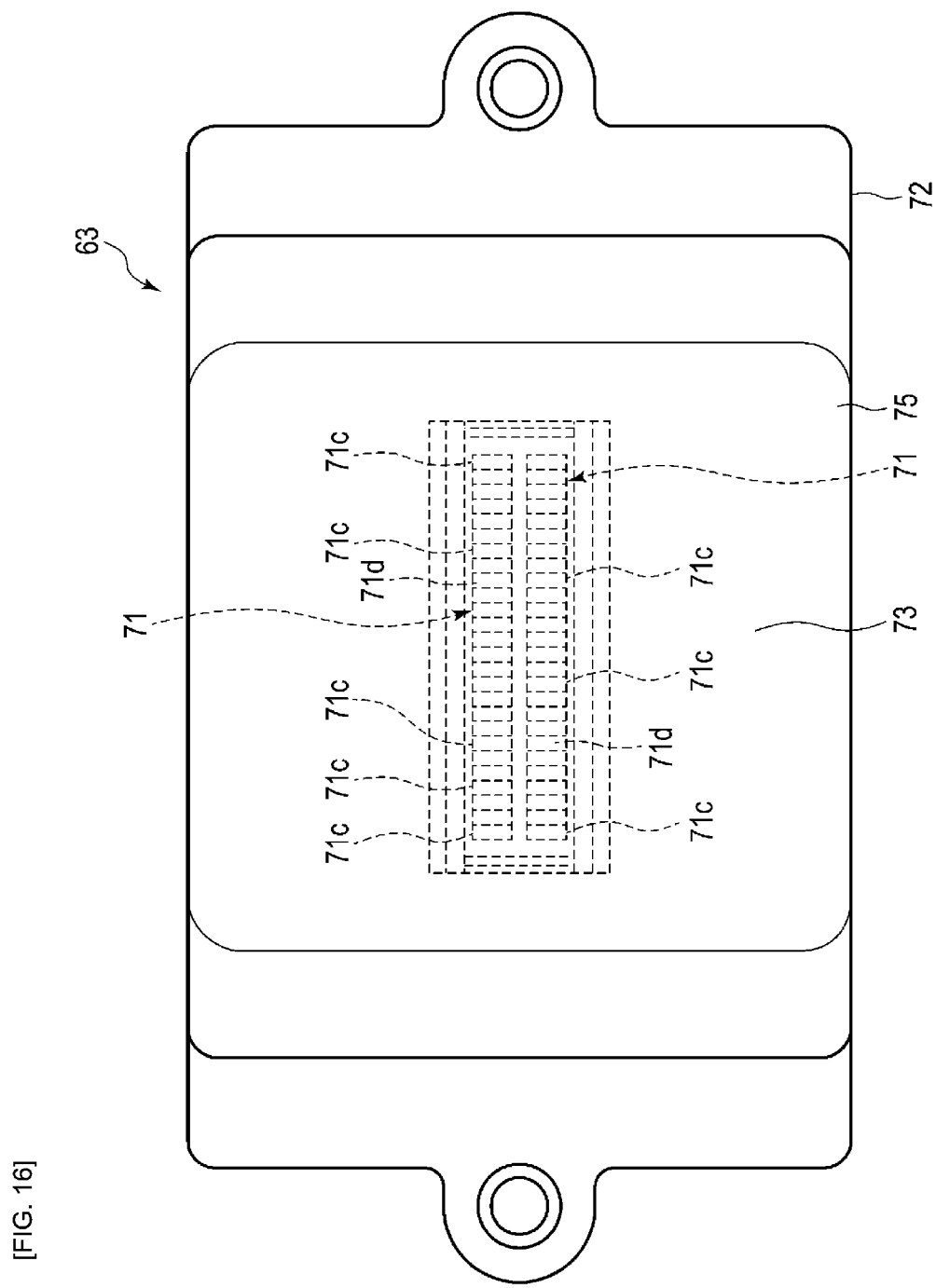
[FIG. 16]

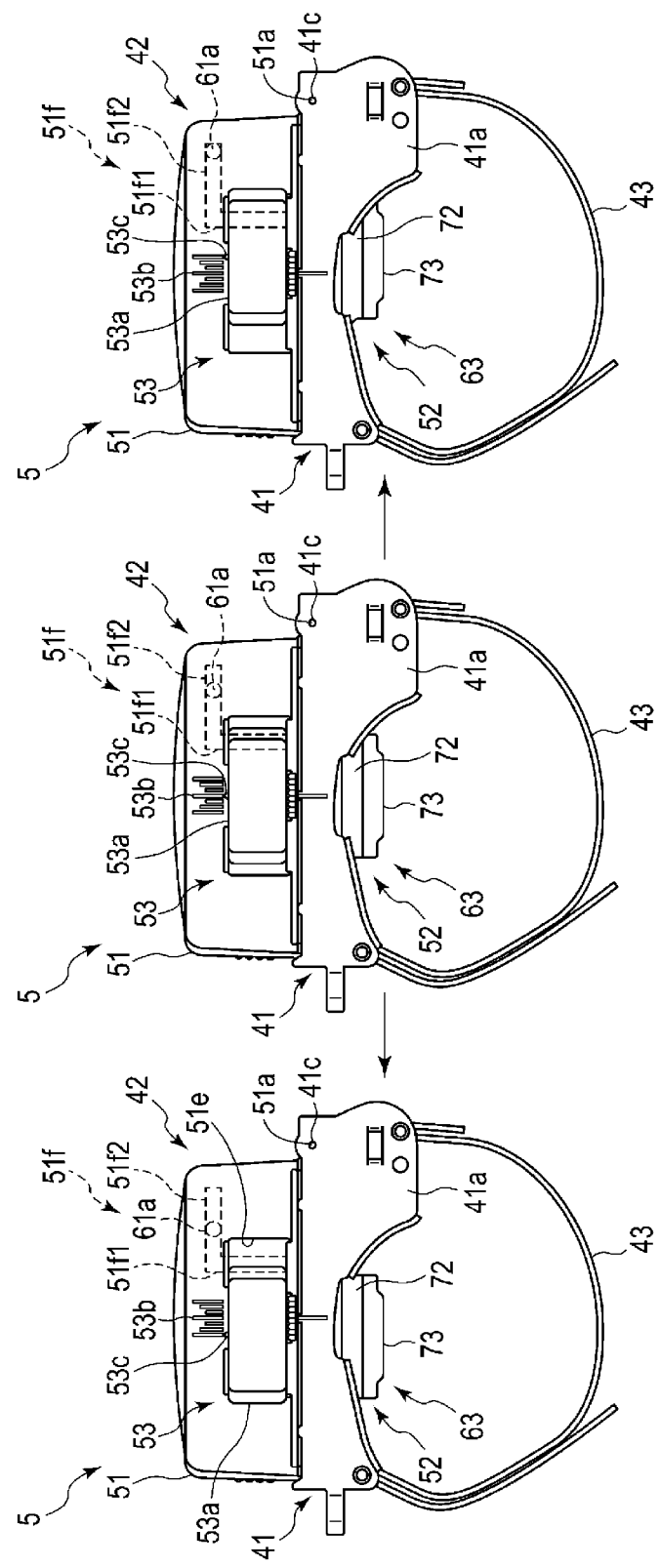

[FIG. 18]
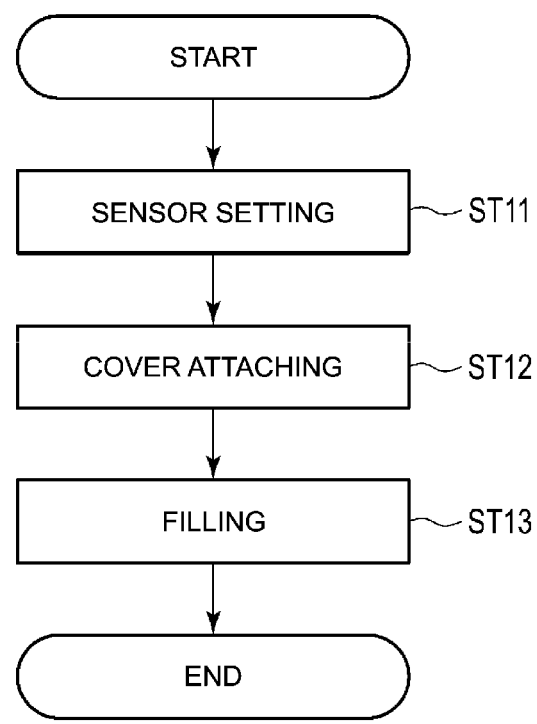

[FIG. 19]
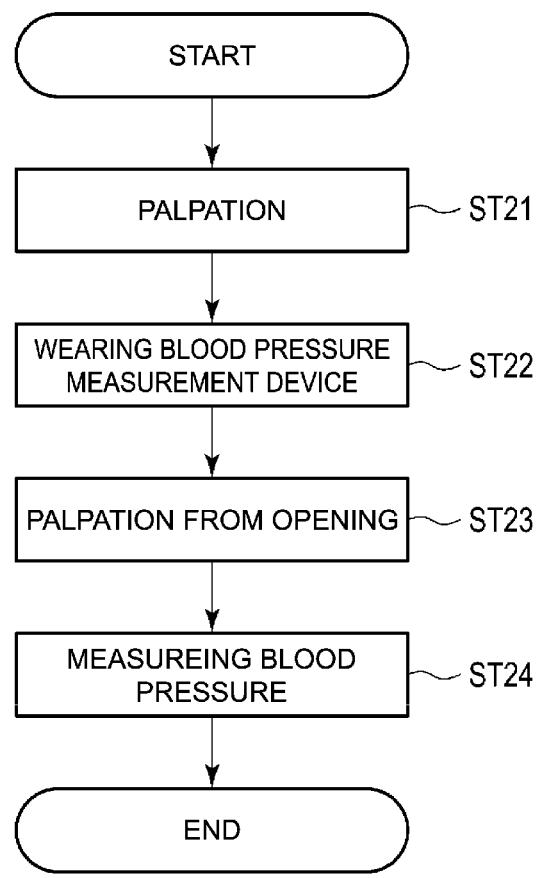

[FIG. 20]
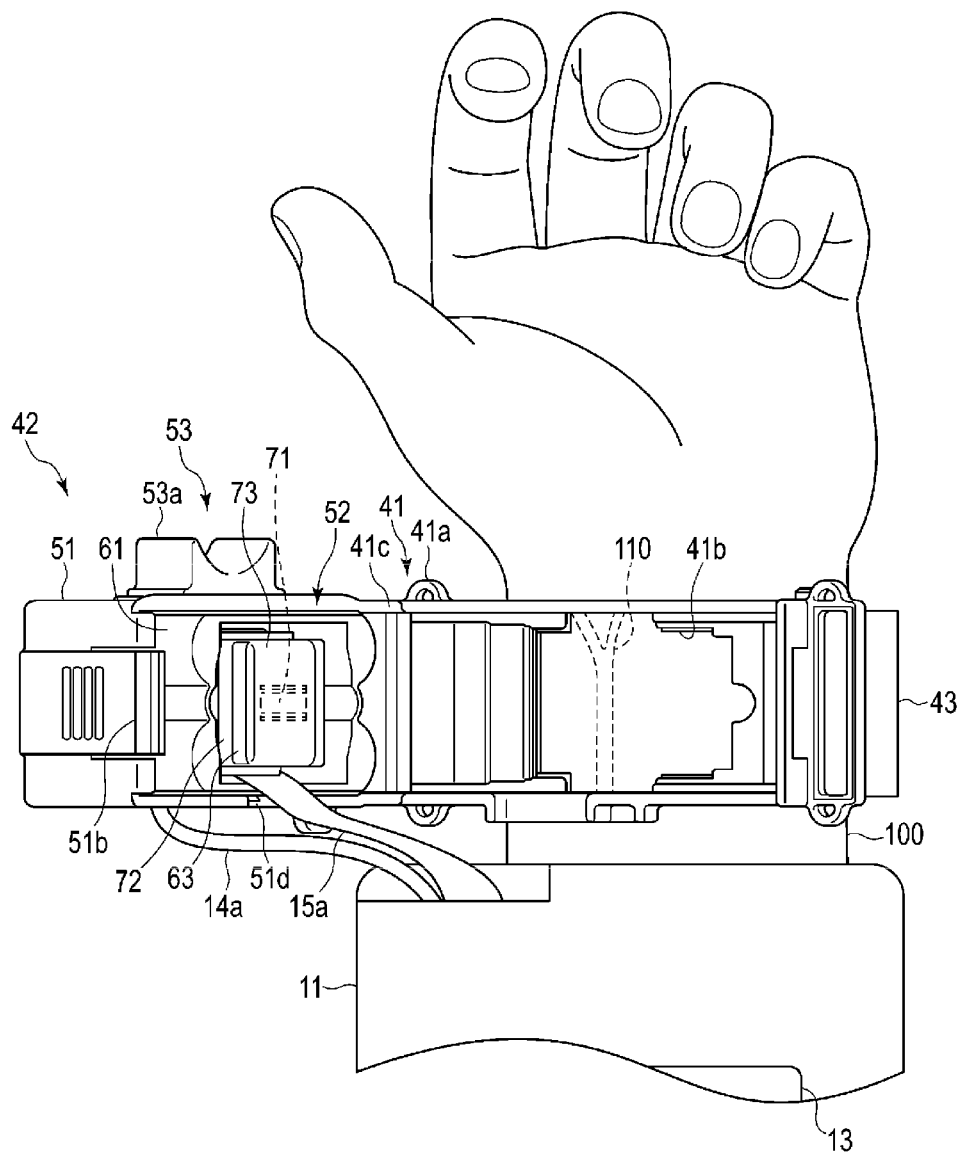

[FIG. 21]
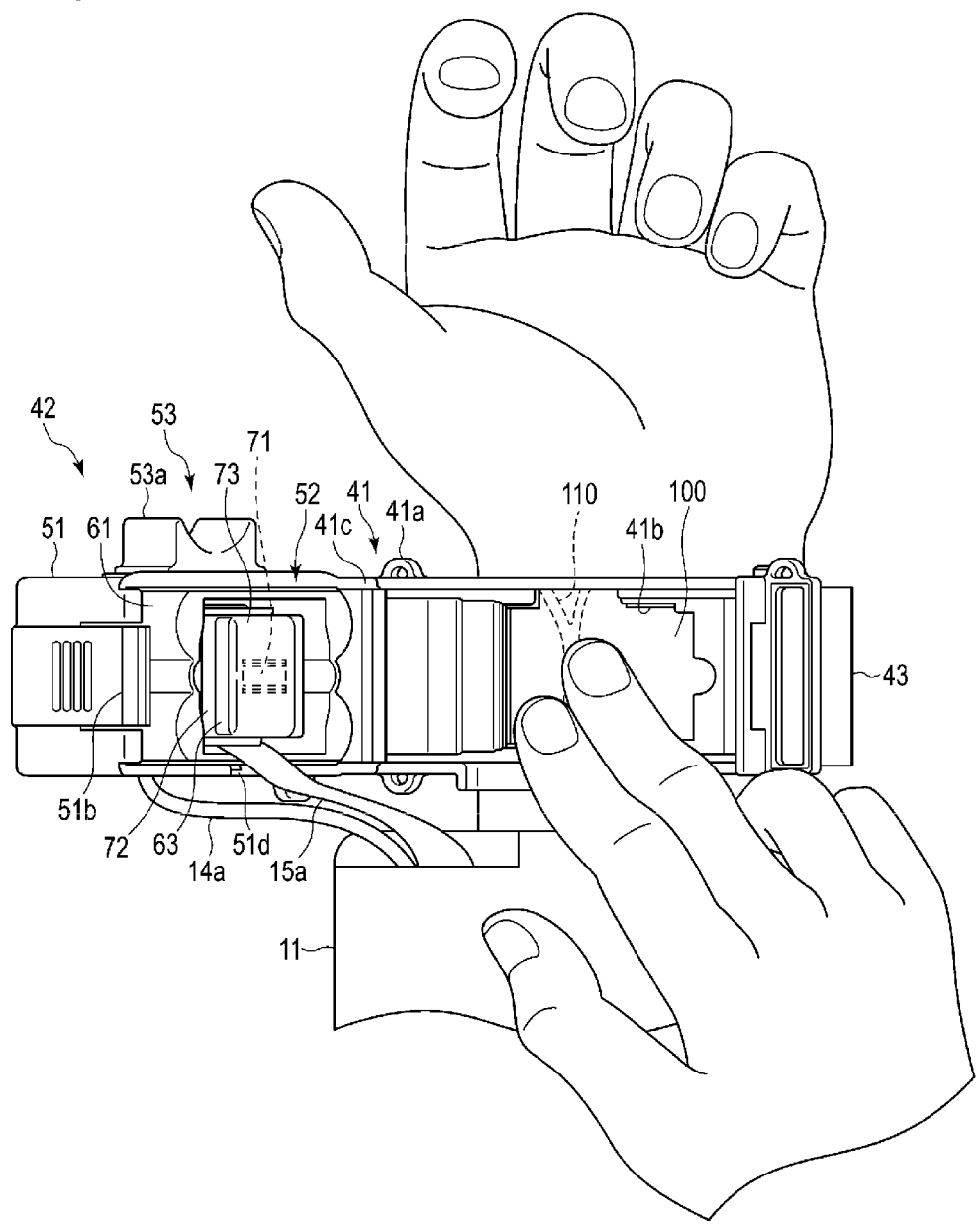

[FIG. 22]
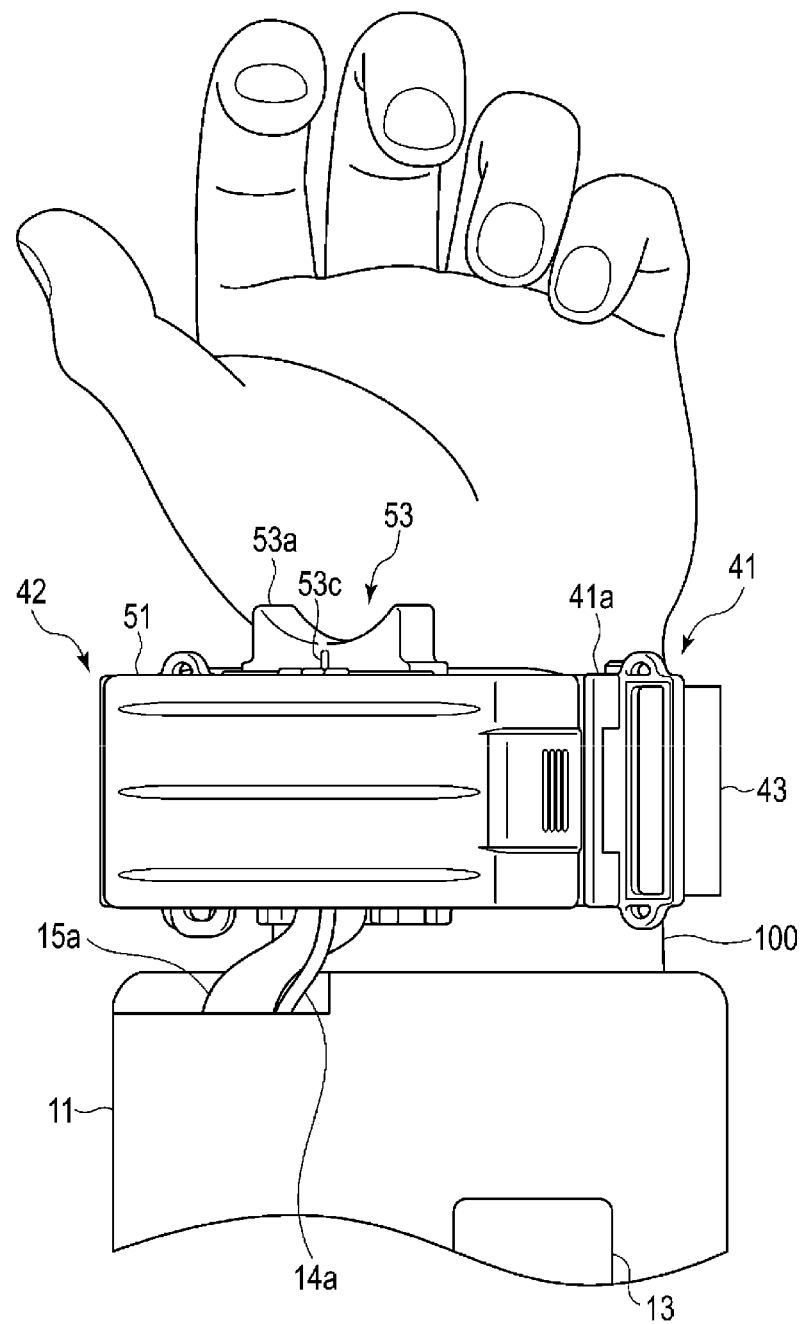

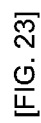
[FIG. 23]

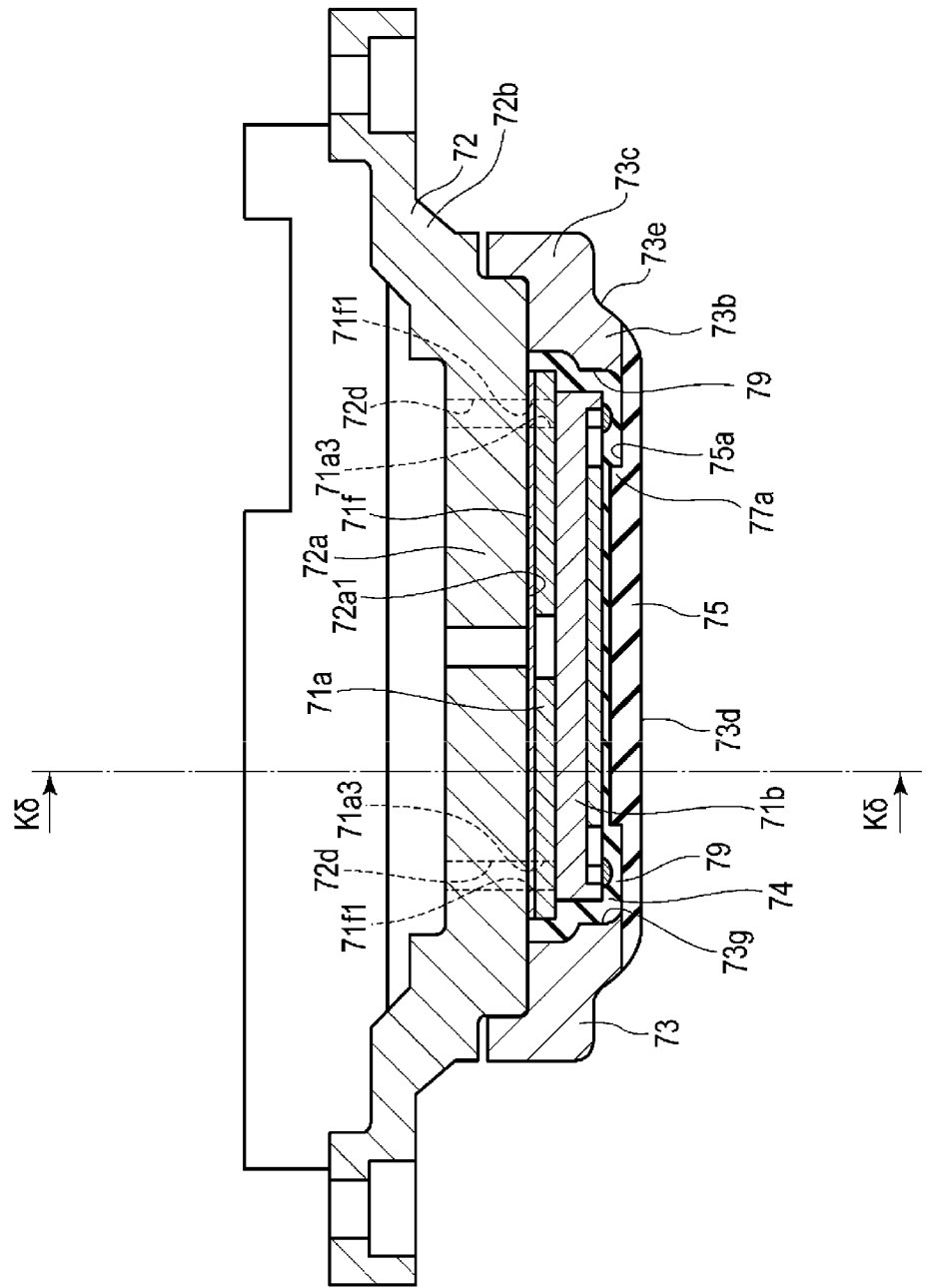

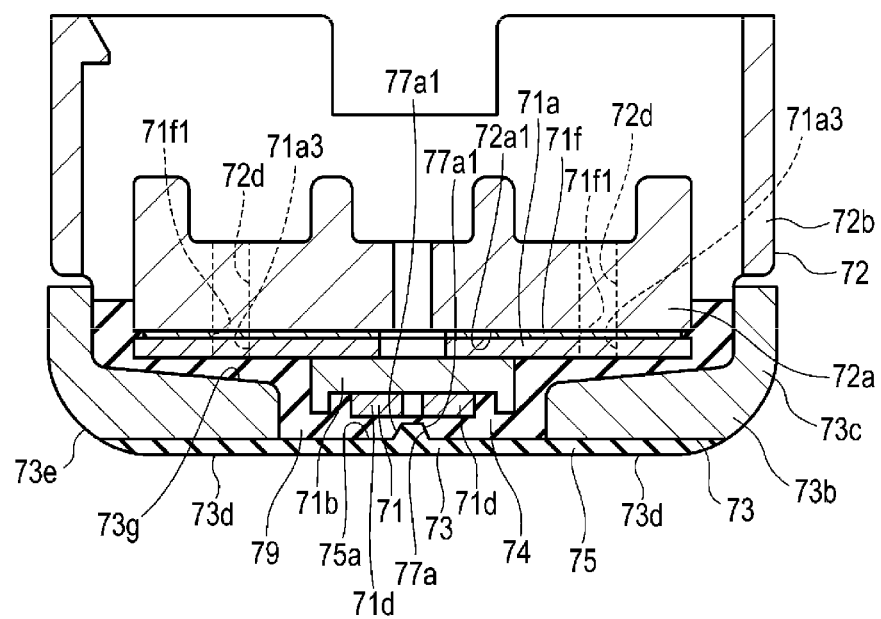
[FIG. 25]

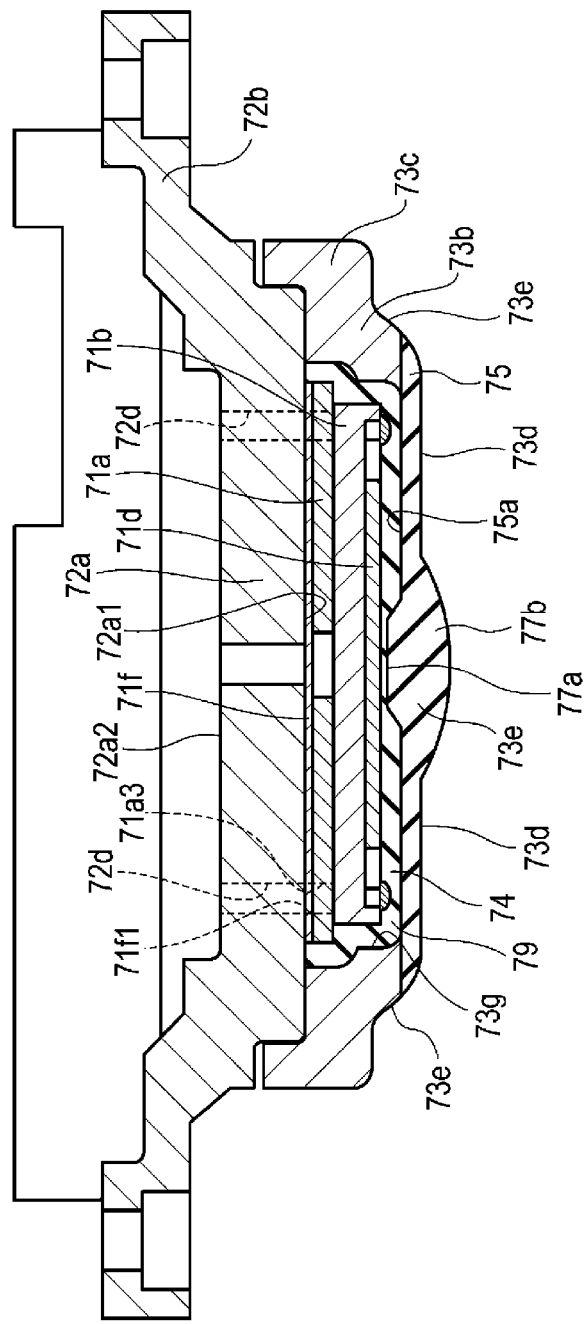
[FIG. 26]

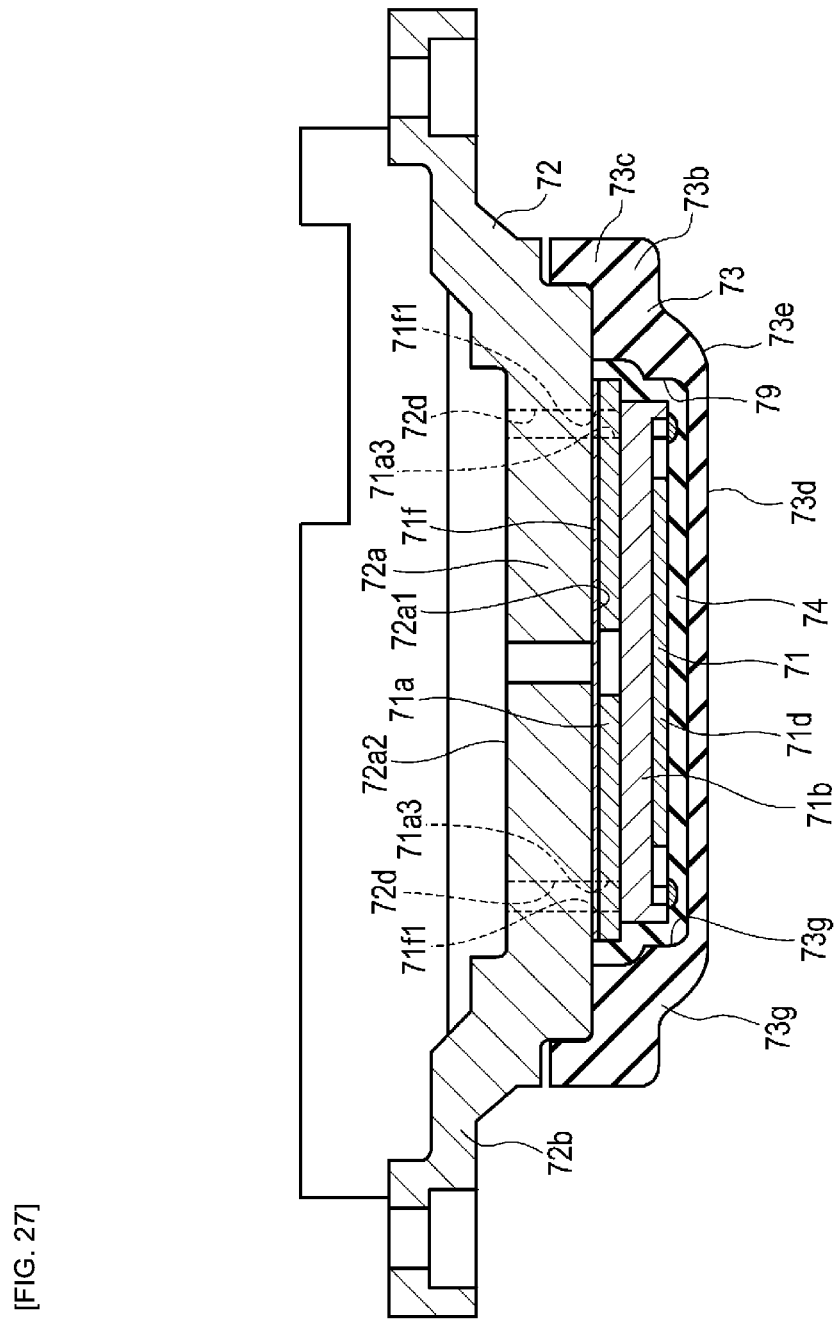
[FIG. 27]

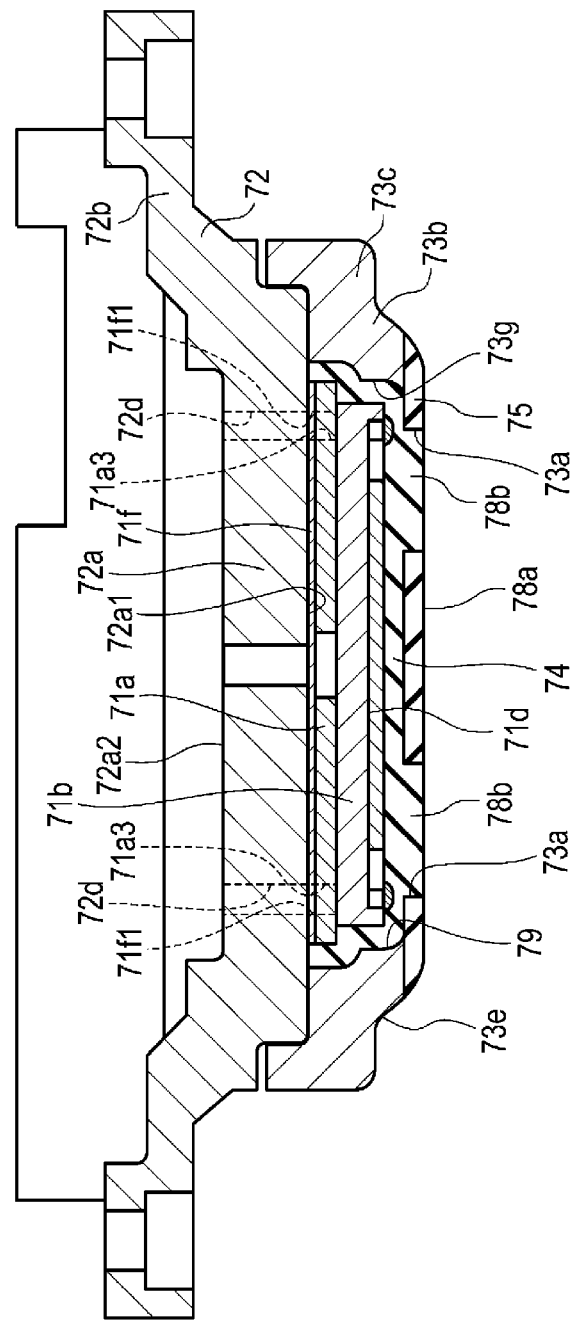
[FIG. 28]

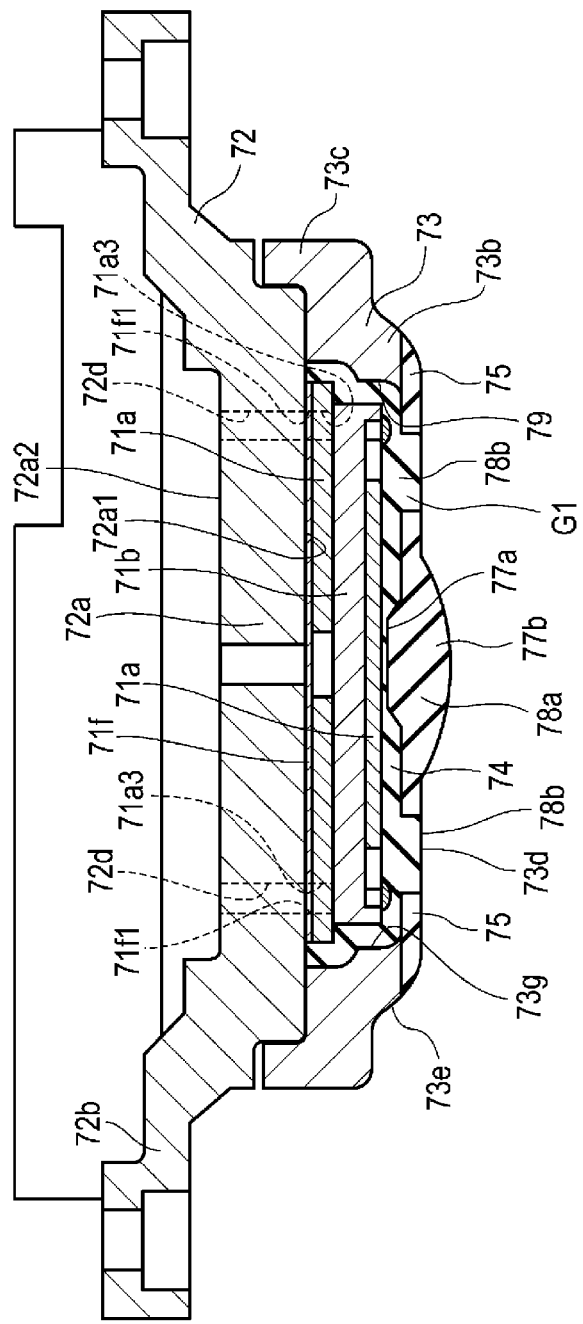
[FIG. 29]

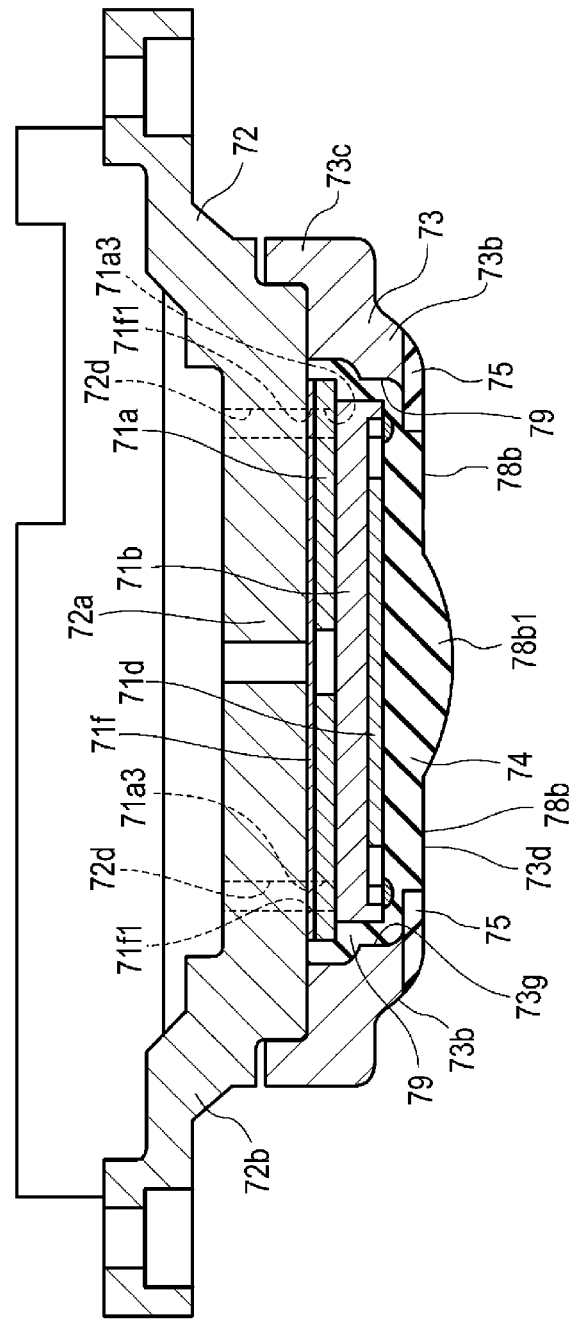
[FIG. 30]

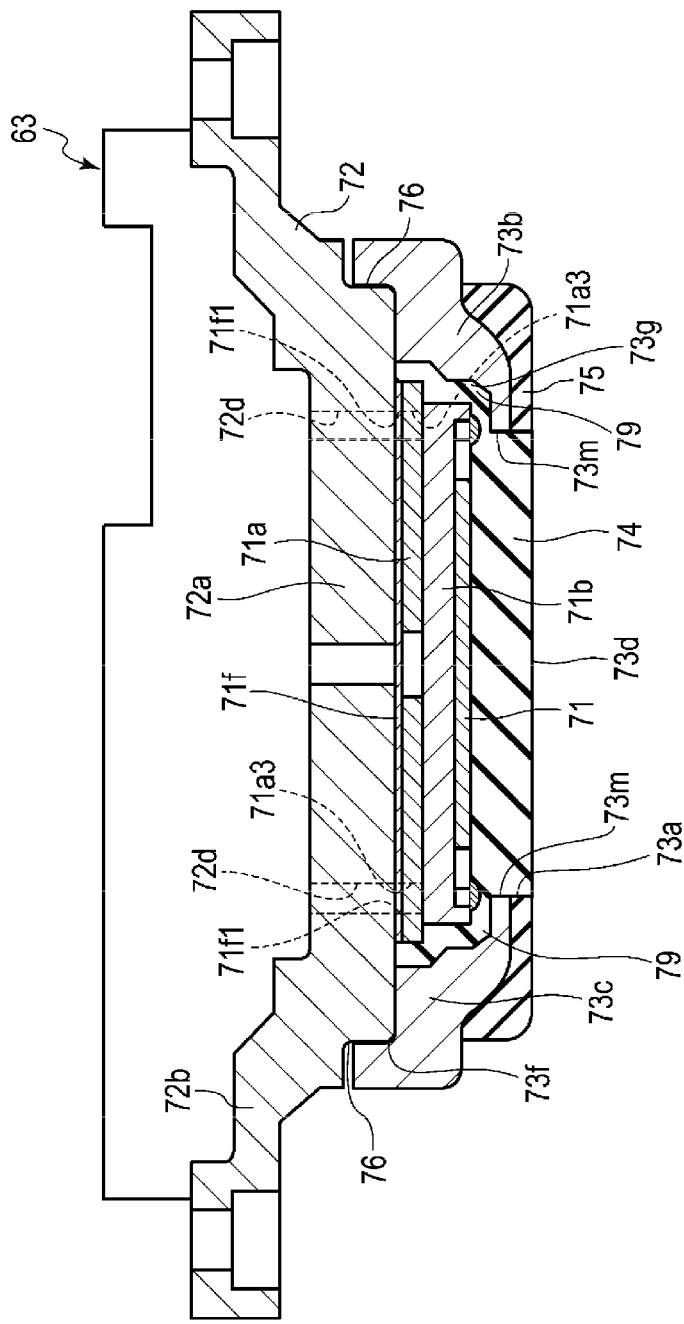
[FIG. 31]

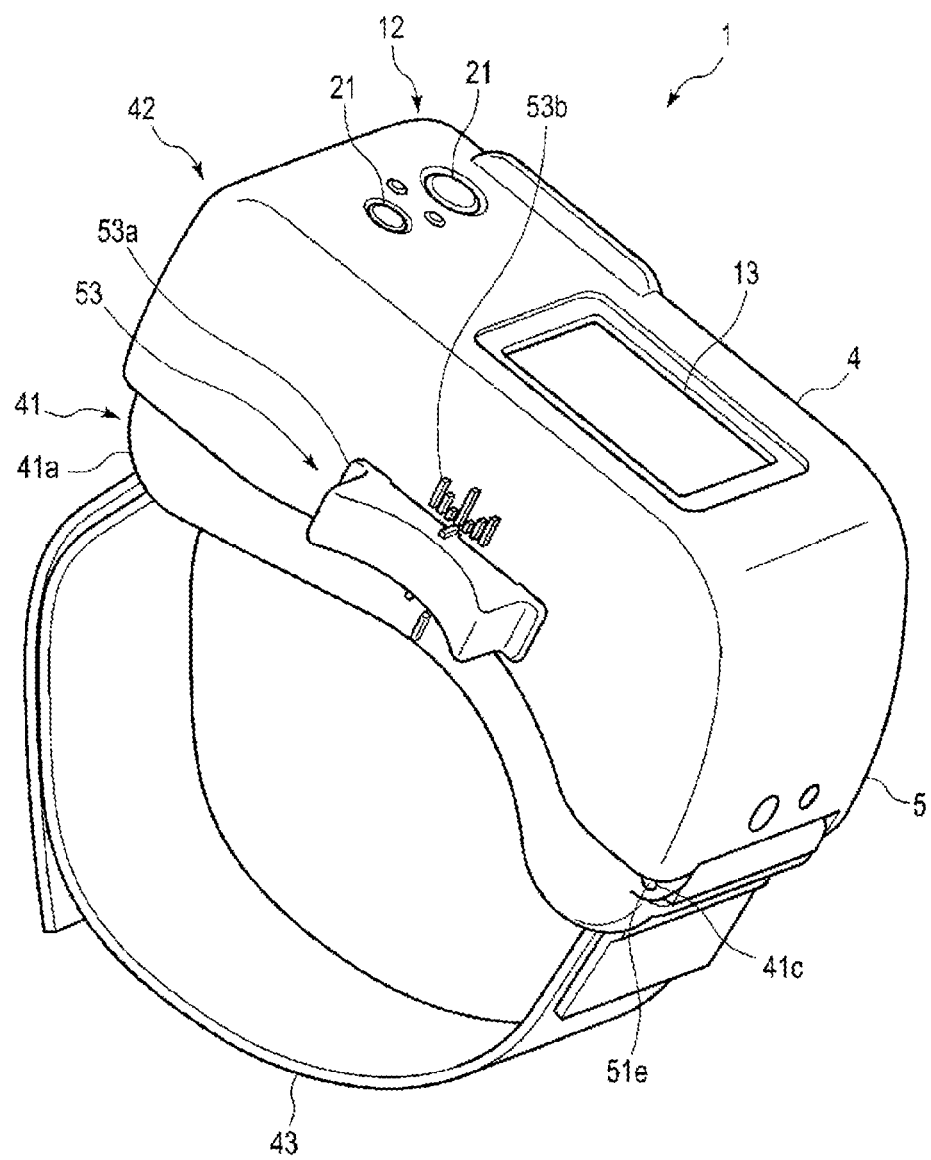
[FIG. 32]

[FIG. 33]
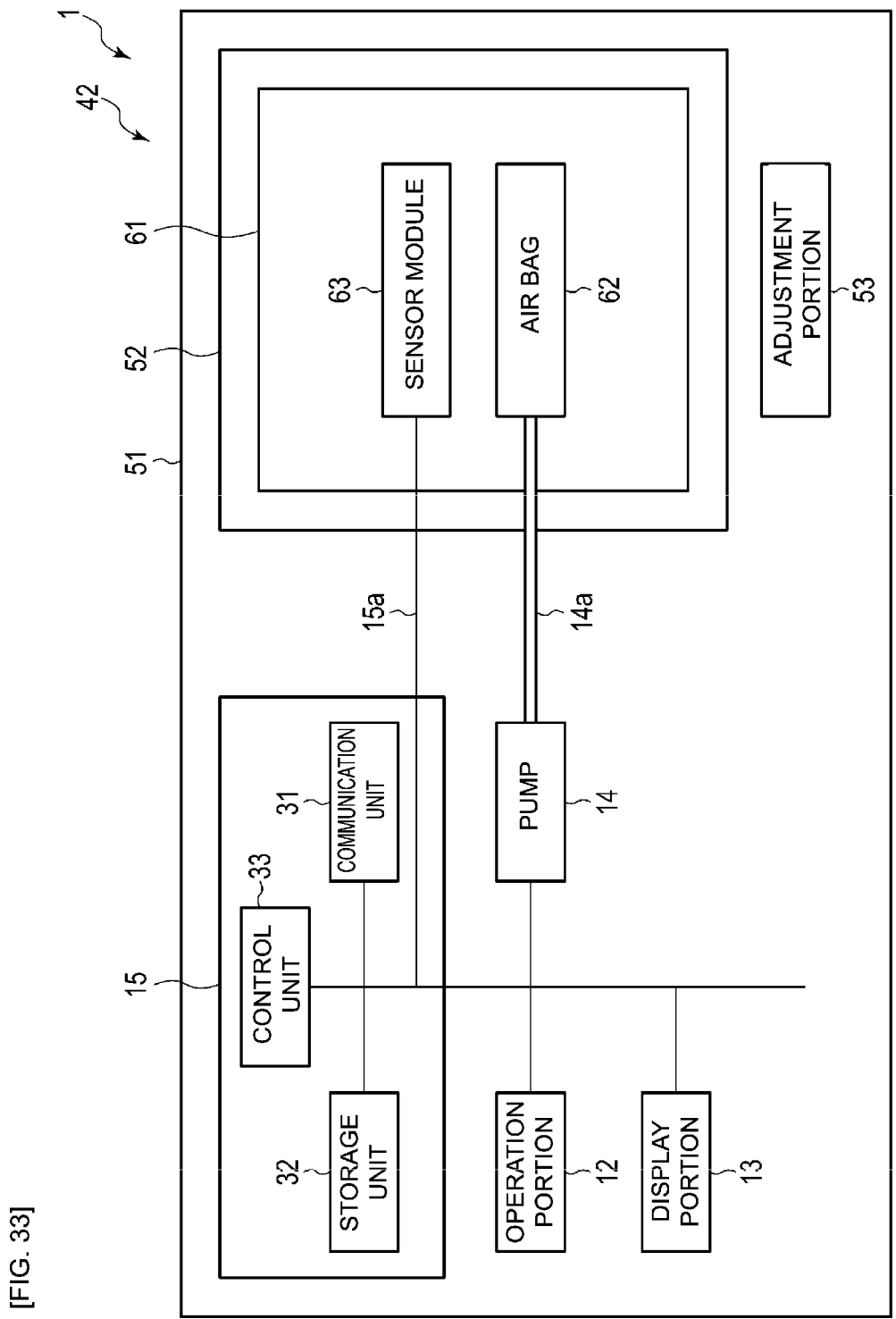

[FIG. 34]
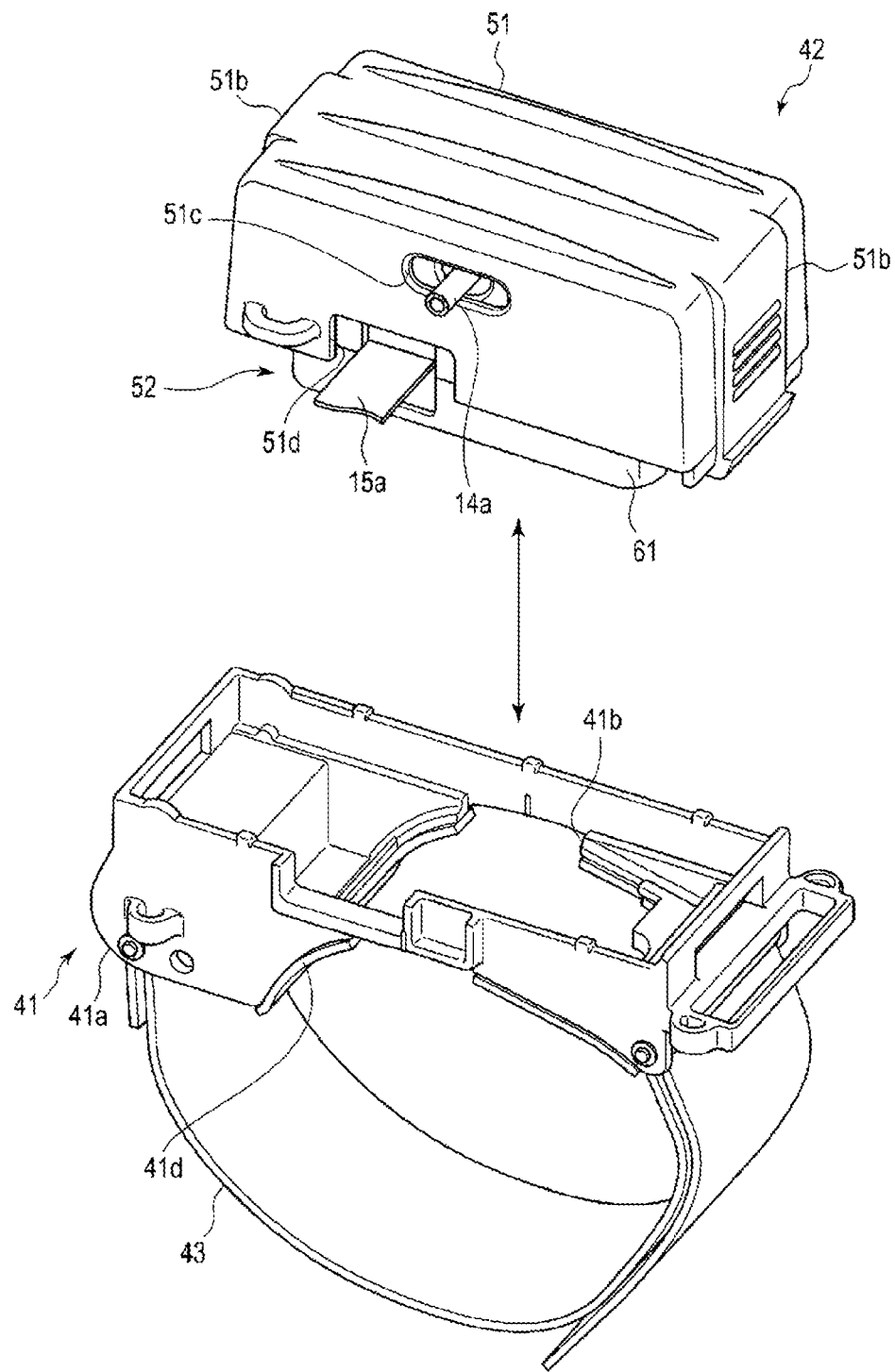

SENSOR MODULE AND BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/020046, filed May 21, 2019 and claiming priority from Japanese Patent Application No. 2018-099726, filed May 24, 2018, which applications are incorporated herein by reference in their entireties.

TECHNICAL FIELD

The present invention relates to a sensor module for measuring the pressure of a living body and a blood pressure measurement device.

BACKGROUND ART

In recent years, blood pressure measurement devices for measuring blood pressure are being used to monitor health status at home, as well as in medical facilities. In such blood pressure measurement devices, for example, known technologies using the oscillometric method and the tonometry method are used. A blood pressure measurement device using the oscillometric method detects vibration of the artery wall and measures blood pressure by using pressure sensor to detect the pressure of a cuff wrapped around the upper arm or wrist of a living body. A blood pressure measurement device using the tonometry method measures blood pressure by bringing a sensor module including a plurality of pressure sensors into contact with the wrist in a region of the wrist where the artery is found.

CITATION LIST

Patent Literature

Patent Document 1: JP H1-288228 A

SUMMARY OF INVENTION

Technical Problem

There is demand for a sensor module that comes into contact with a user when used, such as a sensor module of a blood pressure measurement device that measures blood pressure using the tonometry method, that can improve protection strength of and prevent damage to a surface that comes into contact with the living body.

Thus, an object of the present invention is to provide a sensor module and a blood pressure measurement device that improves the feel felt by a user when in use.

Solution to Problem

An aspect provides a sensor module that includes:
a sensor base;
a pressure sensor portion fixed to the sensor base;
a sensor head cover fixed to the sensor base, the sensor head cover
including a rubber portion that forms, on an outer surface, at least a region that comes into contact with a living body and that allows pressure from the living body to transfer to a side of the pressure sensor portion and forming a gap portion between an inner surface, at least a portion of the inner surface being composed of the rubber portion, and the sensor base and the pressure sensor portion; and
a soft portion disposed in the gap portion at least between the rubber portion and the pressure sensor portion, the soft portion
having a lower hardness than the rubber portion and allowing pressure from the rubber portion to transfer to the pressure sensor portion.

Here, living body is a wrist, for example. The material that forms the rubber portion is a silicone rubber, for example. According to this aspect, the surface that comes into contact with the user of the sensor module is formed from the rubber portion. Thus, the protection strength of the surface of the sensor module that comes into contact with the living body can be improved and damage can be prevented. In addition, because the rubber portion of the sensor head cover comes into contact with the living body, the feel felt by the user when the sensor module comes into contact with the user can be improved.

A sensor module according to the sensor module of the aspect described above may be provided, wherein the pressure sensor portion includes a pressure sensitive element; and a first protrusion portion projecting toward the pressure sensitive element is provided in at least a portion of a region, opposite the pressure sensitive element, of an inner surface of the rubber portion on a side of the pressure sensor portion.

According to this aspect, a portion of the rubber portion is disposed at a position closer to the pressure sensitive element, so the pressure from the living body is efficiently transferred to the pressure sensor portion via the first protrusion portion.

A sensor module according to the sensor module of the aspect described above may be provided, wherein a second protrusion portion projecting toward the living body is provided in at least a portion of a region, opposite the pressure sensor portion, of an outer surface of the rubber portion.

According to this aspect, the pressure of the living body is transferred to the pressure sensor portion more efficiently.

A sensor module according to the sensor module of the aspect described above may be provided, wherein
the sensor head cover includes:
an opening portion formed in a region, opposite the pressure sensor portion, of the sensor base;
a first portion located in the opening portion and formed from an identical material to the rubber portion; and
a second portion located on an outer side of the first portion in the opening portion and formed from an identical material to the soft portion, the second portion closing off space between an edge of the opening portion and the first portion.

According to this aspect, the periphery of the first portion that forms the central portion of the opening portion of the rubber portion is surrounded by the second portion formed from an identical material to the soft portion. According to this configuration, the first portion is supported by the second portion, which has a lower hardness than the first portion. This allows the first portion to easily move toward the pressure sensor portion. Thus, the pressure change of the living body is more easily transmitted to the pressure sensor portion.

A sensor module according to the sensor module of the aspect described above may be provided, wherein the pressure sensor portion includes a pressure sensitive element; and a first protrusion portion projecting toward the pressure sensitive element is provided in at least a portion of a region, opposite the pressure sensitive element, of an inner surface of the first portion on a side of the pressure sensor portion.

According to this aspect, the pressure from the living body is concentrated toward the pressure sensitive element of the pressure sensor portion by the first protrusion portion. Thus, the pressure from the living body is efficiently transmitted to the pressure sensitive element.

A sensor module according to the sensor module of the aspect described above may be provided, wherein the first protrusion portion is configured to have a tapered shape with a cross-sectional area that progressively decreases toward a side of the pressure sensitive element.

Here, the tapered shape with a decreasing cross-sectional area has a cross-sectional shape, along a direction toward the pressure sensitive element side, of a triangle, a trapezoid, or a semicircle.

According to this aspect, the pressure from the living body is further concentrated toward the pressure sensitive element of the pressure sensor portion by the first protrusion portion. Thus, the pressure from the living body is more efficiently transmitted to the pressure sensitive element.

A sensor module according to the sensor module of the aspect described above may be provided, wherein the pressure sensor portion includes a pressure sensitive element array including a plurality of the pressure sensitive elements configured to be arranged side by side; and the first protrusion portion is configured to have a shape that extends in a direction in which the plurality of pressure sensitive element arrays are arranged side by side.

According to this aspect, the pressure from the living body is efficiently concentrated toward the pressure sensitive element array of the pressure sensor portion by the first protrusion portion.

A sensor module according to the sensor module of the aspect described above may be provided, wherein the first portion includes a second protrusion portion projecting toward the living body.

According to this aspect, the pressure from the living body is transferred to the pressure sensor portion more efficiently.

An aspect provides a blood pressure measurement device that includes:

a sensor module including:

a sensor base;

a pressure sensor portion fixed to the sensor base;

a sensor head cover fixed to the sensor base, the sensor head cover including a rubber portion that forms, on an outer surface, at least a region that comes into contact with a living body and that allows pressure from the living body to transfer to a side of the pressure sensor portion and forming a gap portion between an inner surface, at least a portion of the inner surface being composed of the rubber portion, and the sensor base and the pressure sensor portion; and a soft portion disposed in the gap portion at least between the rubber portion and the pressure sensor portion, the soft portion having a lower hardness than the rubber portion and allowing pressure from the rubber portion to transfer to the pressure sensor portion;

an attach portion including an opening portion provided at a position opposite the living body, the sensor module being disposed in the opening portion, and an end surface that curves conforming to a shape in the circumferential direction of a portion of the living body;

a fastener provided on the attach portion; and a case provided on the attach portion, the case housing the sensor module.

According to this aspect, the rubber portion of the sensor head cover comes into contact with the living body. Thus, the protection strength of the surface of the sensor module that comes into contact with the living body can be improved and damage can be prevented.

Advantageous Effects of Invention

The present invention can provide a sensor module and a blood pressure measurement device that improves the protection strength of and prevents damage to a surface of the sensor module that comes into contact with a living body.

BRIEF DESCRIPTION OF DRAWINGS

FIG. 1 is a perspective view illustrating the configuration of a blood pressure measurement device according to an embodiment of the present invention.

FIG. 2 is a block diagram illustrating the configuration of the blood pressure measurement device.

FIG. 3 is a perspective view illustrating the configuration of a sensor device of the blood pressure measurement device.

FIG. 4 is a perspective view illustrating the configuration of a portion of the sensor device of the blood pressure measurement device.

FIG. 5 is a perspective view illustrating the configuration of a sensor unit of the blood pressure measurement device.

FIG. 6 is a plan view illustrating the configuration of the sensor unit.

FIG. 7 is a cross-sectional view illustrating the configuration of a sensor module and an air bag of the sensor unit in a state of taken along a cross-section line VII-VII in FIG. 6.

FIG. 8 is a cross-sectional view illustrating the configuration of the sensor module and the air bag of the sensor unit in a state of taken along a cross-section line VIII-VIII in FIG. 6.

FIG. 9 is a cross-sectional view illustrating the configuration of the sensor module and the air bag of the sensor unit in a state of taken along a cross-section line IX-IX in FIG. 6.

FIG. 10 is a cross-sectional view illustrating the configuration of the blood pressure measurement device.

FIG. 11 is a cross-sectional view illustrating the configuration of the blood pressure measurement device.

FIG. 12 is a cross-sectional view illustrating the configuration of the blood pressure measurement device.

FIG. 13 is a cross-sectional view illustrating the configuration of the sensor module of the sensor unit.

FIG. 14 is a cross-sectional view illustrating the configuration of the sensor module.

FIG. 15 is a perspective view illustrating a sensor base of the sensor module.

FIG. 16 is a plan view illustrating the configuration of the sensor module of the sensor unit.

FIG. 17 is an explanatory diagram illustrating the position adjustment of the sensor unit of the blood pressure measurement device.

FIG. 18 is a flowchart illustrating an example of a method for manufacturing the sensor module.

FIG. 19 is a flowchart illustrating an example of blood pressure measurement using the blood pressure measurement device.

FIG. 20 is an explanatory diagram illustrating an example of blood pressure measurement using the blood pressure measurement device.

FIG. 21 is an explanatory diagram illustrating an example of blood pressure measurement using the blood pressure measurement device.

FIG. 22 is an explanatory diagram illustrating an example of blood pressure measurement using the blood pressure measurement device.

FIG. 23 is a cross-sectional view illustrating the configuration of a sensor module of a blood pressure measurement device according to another embodiment of the present invention.

FIG. 24 is a cross-sectional view illustrating the configuration of the sensor module of the blood pressure measurement device according to another embodiment of the present invention.

FIG. 25 is a cross-sectional view illustrating the configuration of the sensor module.

FIG. 26 is a cross-sectional view illustrating the configuration of a sensor module of a blood pressure measurement device according to another embodiment of the present invention.

FIG. 27 is a cross-sectional view illustrating the configuration of a sensor module of a blood pressure measurement device according to another embodiment of the present invention.

FIG. 28 is a cross-sectional view illustrating the configuration of a sensor module of a blood pressure measurement device according to another embodiment of the present invention.

FIG. 29 is a cross-sectional view illustrating the configuration of a sensor module of a blood pressure measurement device according to another embodiment of the present invention.

FIG. 30 is a cross-sectional view illustrating the configuration of a sensor module of a blood pressure measurement device according to another embodiment of the present invention.

FIG. 31 is a cross-sectional view illustrating the configuration of a sensor module of a blood pressure measurement device according to another embodiment of the present invention.

FIG. 32 is a perspective view illustrating the configuration of a blood pressure measurement device according to another embodiment of the present invention.

FIG. 33 is a block diagram illustrating the configuration of the blood pressure measurement device.

FIG. 34 is a perspective view illustrating the configuration of a blood pressure measurement device according to another embodiment of the present invention.

DESCRIPTION OF EMBODIMENTS

First Embodiment

An example of a blood pressure measurement device 1 according to the first embodiment of the present invention is described below using FIGS. 1 to 16.

FIG. 1 is a perspective view illustrating the configuration of the blood pressure measurement device 1 according to an embodiment of the present invention in a state in which a body fastener 16 is closed. FIG. 2 is a block diagram illustrating the configuration of the blood pressure measurement device 1. FIG. 3 is a perspective view illustrating the configuration of a sensor device 5 of the blood pressure measurement device 1 in a state in which a sensing body 42 is open. FIG. 4 is a perspective view illustrating the configuration of the blood pressure measurement device 1 with a sensor unit 52 removed from the sensor device 5. FIG. 5 is a perspective view illustrating the configuration of the sensor unit 52 of the blood pressure measurement device 1.

FIG. 6 is a plan view illustrating the configuration of the sensor unit 52. FIG. 7 is a cross-sectional view illustrating the configuration of a sensor module 63 and an air bag 62 of the sensor unit 52 in a state of taken along a cross-section line VII-VII in FIG. 6. FIG. 8 is a cross-sectional view illustrating the configuration of the sensor module 63 and the air bag 62 of the sensor unit 52 in a state of taken along a cross-section line VIII-VIII in FIG. 6. FIG. 9 is a cross-sectional view illustrating the configuration of the sensor module 63 and the air bag 62 of the sensor unit 52 in a state of taken along a cross-section line IX-IX in FIG. 6.

FIG. 10 is a cross-sectional view illustrating the configuration of the blood pressure measurement device 1. FIG. 11 is a cross-sectional view illustrating the configuration of the blood pressure measurement device 1. FIG. 12 is a cross-sectional view illustrating the configuration of the blood pressure measurement device 1. FIG. 13 is a cross-sectional view illustrating the configuration of the sensor module 63 of the sensor unit 52 in a state of taken along a cross-section aligned with the direction that pressure sensitive elements 71c of a pressure sensor portion 71 are arranged side by side. FIG. 14 is a cross-sectional view illustrating the configuration of the sensor module 63 in a state of taken along a cross-section orthogonal to the direction that pressure sensitive elements 71c are arranged side by side. FIG. 15 is a perspective view illustrating a sensor base 72 of the sensor module 63. FIG. 16 is a plan view illustrating the configuration of the sensor module 63 of the sensor unit 52.

Note that in the drawings, a radial artery of a wrist 100 is denoted as 110, a radius is denoted as 111, an ulnar artery is denoted as 112, an ulna is denoted as 113, and a tendon is denoted as 114.

The blood pressure measurement device 1 is an electronic blood pressure measurement device that is attached to the wrist 100 of a living body and calculates a blood pressure value from the pressure of the radial artery 110. As illustrated in FIGS. 1 to 16, the blood pressure measurement device 1 includes a device body 4 and the sensor device 5. For example, the blood pressure measurement device 1 has a configuration in which the sensor device 5 is attached to a region of the wrist 100 where the radial artery 110 is found and in which the device body 4 is attached to the wrist 100 adjacent to the sensor device 5 on the elbow side.

The blood pressure measurement device 1, by pressing the radial artery 110 with the sensor device 5, measures the pressure of the pressure pulse wave per heart beat that changes in conjunction with the heart rate of the radial artery 110, executes, via the device body 4, processing based on the tonometry method on the measured pressure, and obtains the blood pressure.

As illustrated in FIGS. 1 and 2, the device body 4 includes: a body case 11, an operation portion 12, a display portion 13, a pump 14, a control board 15, and the body fastener 16. Also, for example, the device body 4 may be provided with a cuff on the body fastener 16 that is configured to compress the wrist 100 during blood pressure measurement.

The body case 11 houses: a portion of the operation portion 12, a portion of the display portion 13, and the control board 15 and exposes: a portion of the operation portion 12 and a portion of the display portion 13 from the outer surface. In addition, the body fastener 16 is attached to the body case 11.

The operation portion 12 is configured to receive an instruction input from a user. For example, the operation portion 12 includes: a plurality of buttons 21 provided on the body case 11 and a sensor that detects operation of the buttons 21. Note that the operation portion 12 may be provided on the display portion 13 as a touch panel. When operated by the user, the operation portion 12 converts an instruction into an electrical signal. The sensor that detects operation of the buttons 21 is electrically connected to the control board 15 and outputs an electrical signal to the control board 15.

The display portion 13 is disposed in the body case 11 and is exposed from the outer surface of the body case 11. The display portion 13 is electrically connected to the control board 15. The display portion 13 is, for example, a liquid crystal display or an organic electroluminescent display. The display portion 13 displays various information including measurement results such as date and time; blood pressure values like maximum blood pressure and minimum blood pressure; heart rate; and the like.

The pump 14 is, for example, a piezoelectric pump. The pump 14 includes a tube 14a connected to the sensor device 5 for compressing air and supplying compressed air to the sensor device 5 via the tube 14a. The pump 14 is electrically connected to the control board 15.

As illustrated in FIG. 2, the control board 15 includes a communication unit 31, a storage unit 32, and a control unit 33, for example. The control board 15 is configured by the communication unit 31, the storage unit 32, and the control unit 33 being mounted on the board. Also, the control board 15 is connected to the sensor device 5 via a cable 15a. The cable 15a runs from inside the body case 11 to outside the body case 11 via a portion of the outer surface of the body case 11. For example, the cable 15a runs from inside the body case 11 to the sensor device 5 via an opening formed in a side surface of the body case 11.

The communication unit 31 is configured to transmit and receive information from an external device wirelessly or via a wire. The communication unit 31 transmits information, such as information controlled by the control unit 33, measured blood pressure values, pulse, and the like, to an external device via a network and receives a program for software update or the like from an external device via a network and sends this to the control unit.

In the present embodiment, the network is, for example, the Internet, but no such limitation is intended. The network may be a network such as a Local Area Network (LAN) provided in a hospital or may be a direct wired communication with an external device, using a cable or the like including terminals of a predetermined protocol such as USB. Thus, the communication unit 31 may include a plurality of wireless antennas, micro-USB connectors, or the like.

The storage unit 32 pre-stores: program data for controlling the entire blood pressure measurement device 1; settings data for configuring various functions of the blood pressure measurement device 1; calculation data for calculating blood pressure values and pulse from the pressure measured by the pressure sensitive elements 71c, and the like. Furthermore, the storage unit 32 stores information such as: the calculated blood pressure value; pulse; time series data in which this calculated data and time are associated; and the like.

The control unit 33 is composed of, for example, a single or a plurality of central processing units (CPU), controls the operation of the entire blood pressure measurement device 1, and executes each processing on the basis of the program data. The control unit 33 is electrically connected to the operation portion 12, the display portion 13, the pump 14, and the sensor device 5, controls the operation of each configuration, transmits and receive signals, and supplies power.

The body fastener 16 includes, for example, one or a plurality of band-like bands; and a fixing member such as a hook-and-loop fastener that secures the band wrapped around the wrist 100. The body fastener 16 fixes the body case 11 to the wrist 100.

With the device body 4 having such a configuration, by the control unit 33 executing processing using the program data stored in the storage unit 32, blood pressure data can be continuously generated from the pulse waves of the radial artery 110 detected by the sensor device 5. The blood pressure data includes data of blood pressure waveforms corresponding to the waveforms of measured pulse waves. The blood pressure data may further include time series data of a blood pressure feature value (blood pressure value). The blood pressure feature value includes, for example and without limitation, systolic blood pressure (SBP) and diastolic blood pressure (DBP). The maximum value in the pulse wave waveform per heart beat corresponds to systolic blood pressure, and the minimum value in the pulse wave waveform of per heart beat corresponds to diastolic blood pressure.

In this embodiment, the device body 4 measures the pressure pulse wave as a pulse wave by the tonometry method. Here, the tonometry method refers to a method for pressing the radial artery 110 from above the skin with appropriate pressure, forming a flat portion in the artery, and measuring the pressure pulse wave with the sensor device 5 in a balanced state between the interior and the exterior of the radial artery 110. According to the tonometry method, a blood pressure value per heart beat can be acquired.

As illustrated in FIGS. 1, 3, and 4, the sensor device 5 includes: an attach portion 41, the sensing body 42, and a fastener 43.

The attach portion 41 includes a main surface that has a shape that conforms to the circumferential direction of the wrist 100 in the region where the radial artery 110 of the left wrist 100 is found. As a specific example, the attach portion 41 includes: a base portion 41a that curves conforming to the shape in the circumferential direction of the wrist 100 in the region in contact with the wrist 100; an opening portion 41b formed in the base portion 41a, an attachment portion 41c provided on the base portion 41a for attaching the sensing body 42; and a cushion 41d provided on a main surface of the base portion 41a that comes into contact with the wrist 100.

The base portion 41a is configured to be elongated in one direction. The base portion 41a is disposed on a palm side of wrist 100 and on a side portion side on the radius 111 side of the wrist 100, and the main surface disposed on the wrist 100 side curves conforming to the shape in the circumferential direction of the palm side of the wrist 100 and the side portion side on the radius 111 side of the wrist 100. Furthermore, at least the outer circumferential edge side of the main surface of the base portion 41a comes into contact with the sensing body 42.

The opening portion 41b is provided in a central region of the base portion 41a and is formed with a size of one or a plurality of fingers. That is, the opening portion 41b is formed with a size that allows the region where the radial artery 110 of the wrist 100 is exposed from the opening portion 41b to be palpated by a finger, when the sensor device 5 is attached to the wrist 100, and that allows a portion of the sensing body 42 to come into contact with the wrist 100.

The attachment portion 41c is provided on a main surface of the base portion 41a opposite the surface facing the wrist 100 and provided on an end side of the base portion 41a in the longitudinal direction. The attachment portion 41c supports the sensing body 42 and is configured to move the sensing body 42 in a direction away from the base portion 41a and a direction toward the base portion 41a. As a specific example, the attachment portion 41c is a journal-like portion that rotatably journals the sensing body 42 about an axis. For example, the attachment portion 41c is integrally formed with the base portion 41a.

The cushion 41d is, for example, an elastic body configured in a sheet shape from a foaming resin material provided on a main surface of the base portion 41a that comes into contact with the wrist 100. The cushion 41d protects wrist 100 by elastically deforming, for example, when the blood pressure measurement device 1 is worn on the wrist 100.

As illustrated in FIGS. 2 to 12, the sensing body 42 includes: a case 51, the sensor unit 52, and an adjustment portion 53 for adjusting the position of the sensor unit 52.

The case 51 has a rectangular box shape with an open surface opposite the attach portion 41, for example. The case 51 supports the sensor unit 52 and the adjustment portion 53. Furthermore, the case 51 is attached to the attachment portion 41c in a manner to be movable back and forth in a direction away from the base portion 41a. As a specific example, the case 51 includes a rotation shaft 51a rotatably disposed in the attachment portion 41c. Also, the case 51 includes an engagement portion 51b that fixes the case 51 to the base portion 41a when it comes into contact with the base portion 41a. The engagement portion 51b, for example, is a projection that engages with an opening provided on the base portion 41a and, by being operated, is configured to release the engagement with the opening of the base portion 41a.

Furthermore, the case 51 includes: a first hole portion 51c where the tube 14a is disposed, a second hole portion 51d where the cable 15a is disposed, a third hole portion 51e that movably supports a portion of the adjustment portion 53, and a guide groove 51f that guides the movement of the sensor unit 52.

The first hole portion 51c and the second hole portion 51d are provided on the same side wall of the case 51 adjacent to the device body 4 when the device is worn on the wrist 100.

The third hole portion 51e is provided on a side wall opposite to the side wall of the case 51 where the first hole portion 51c and the second hole portion 51d are provided. The third hole portion 51e is a rectangular opening that linearly extends in the longitudinal direction of the case 51, or in other words, the circumferential direction of the wrist 100 when the sensor device 5 is attached to the wrist 100.

The guide groove 51f is provided on the inner surface side of the side wall of the case 51 provided with the third hole portion 51e. The guide groove 51f includes: a first groove 51f1 that extends from an opening end portion of the case 51 to partway toward the ceiling opposite the opening; and a second groove 51f2 that extends in a direction orthogonal to the first groove 51f1. The second groove 51f2 connects to the first groove 51f1 at one end and extends from this end to the other end toward one side in the longitudinal direction of the case 51.

The sensor unit 52 includes: a movable case 61, the air bag 62, the sensor module 63, and a movable base 64 that supports the sensor module 63 to be movable in one direction with respect to the movable case 61. The sensor unit 52 is supported by the case 51 in a manner to be movable in a predetermined range in the longitudinal direction of the case 51 via the adjustment portion 53.

The movable case 61 houses the sensor module 63 and the movable base 64 and supports the movable base 64 supporting the sensor module 63 in a manner allowing the movable base 64 to be movable toward the opening portion 41b of the attach portion 41. The movable case 61 is supported in a manner to be movable in the longitudinal direction of the case 51 inside the case 51.

As a specific example, the movable case 61 has a rectangular box shape with the surface opposite the attach portion 41 housing the air bag 62 and the sensor module 63 being open. The movable case 61 houses the air bag 62, the sensor module 63, and the movable base 64. In the movable case 61, the air bag 62 is disposed between the ceiling and the movable base 64. The movable case 61 supports the movable base 64 in a manner allowing the movable base 64 to be movable in one direction so that the sensor module 63 can protrude out from the opening of the movable case 61.

The movable case 61 includes: a guide projection 61a disposed on the outer surface of a side wall opposite the side wall on which the guide groove 51f of the case 51 is provided in a manner allowing the guide projection 61a to move in the guide groove 51f; and a fixing portion 61b in which a portion of the adjustment portion 53 is fixed. As the guide projection 61a moves in the second groove 51f2, the movable case 61 moves in the longitudinal direction of the case 51.

The air bag 62 has a bellows-like structure. The air bag 62 is fluidly connected to the pump 14 via the tube 14a. As illustrated in FIGS. 7 to 12, the air bag 62 expands in a direction from the ceiling of the movable case 61 toward the opening. When the air bag 62 expands, the sensor module 63 is moved from a position where the sensor module 63 is housed within the movable case 61 to a position where the sensor module 63 projects from the opening of the movable case 61 and comes into contact with the wrist 100 via the opening portion 41b of the attach portion 41. The air bag 62 is formed from polyurethane, for example.

As illustrated in FIGS. 13, 14, and 16, the sensor module 63 includes: the pressure sensor portion 71, the sensor base 72 that supports the pressure sensor portion 71, a sensor head cover 73 that covers the sensor base 72, and a soft portion 74.

The sensor module 63 is disposed inside the movable case 61 and is supported by the movable case 61 in a manner allowing the sensor module 63 to move in a predetermined movement range in the direction of the ceiling and the opening of the movable case 61 opposing one another. In other words, the sensor module 63 is supported in a manner to be movable within the movable case 61, and the movement is restricted by a restriction portion such as a stopper or like when the sensor module 63 moves from the opening of the movable case 61 to the position where the sensor module 63 projects out a certain amount or more.

The pressure sensor portion 71 includes: a flexible substrate 71a, a substrate 71b mounted on the flexible substrate 71a, and the plurality of pressure sensitive elements 71c mounted on the substrate 71b. The pressure sensor portion 71 is fixed on one main surface of the sensor base 72.

The flexible substrate 71a is adhered and fixed on the sensor base 72 via an adhesive sheet 71f, for example. A predetermined circuit pattern is formed on one main surface of the flexible substrate 71a. The substrate 71b is mounted on the flexible substrate 71a. The cable 15a is connected to the circuit pattern of the flexible substrate 71a. The cable 15a is composed of a flexible substrate, for example. In other words, the flexible substrate 71a is electrically connected to the control board 15 via the cable 15a.

The substrate 71b is electrically connected to the flexible substrate 71a. The substrate 71b is electrically connected to the control board 15 via the flexible substrate 71a and the cable 15a. The substrate 71b has a rectangular plate-like shape.

The plurality of pressure sensitive elements 71c are mounted on the substrate 71b. The plurality of pressure sensitive elements 71c are electrically connected to the circuit pattern on the flexible substrate 71a. In other words, the plurality of pressure sensitive elements 71c are electrically connected to the control board 15 via the substrate 71b, the flexible substrate 71a, and the cable 15a.

The substrate 71b and the plurality of pressure sensitive elements 71c constitute a sensor chip. The plurality of pressure sensitive elements 71c are arranged in one direction, forming a pressure sensitive element array 71d.

A single or a plurality of the pressure sensitive element arrays 71d are provided. In the case in which a plurality of the pressure sensitive element arrays 71d are provided, the plurality of pressure sensitive element arrays 71d are disposed at predetermined intervals in a direction orthogonal to the arrangement direction of the plurality of pressure sensitive element arrays 71d. In the present embodiment, two rows of the pressure sensitive element arrays 71d are formed.

Also, the pressure sensor portion 71 is disposed in the sensor base 72 such that the direction in which the plurality of pressure sensitive elements 71c are arranged is the width direction of the wrist 100. The pressure sensor portion 71 transmits a pressure value measured by the plurality of pressure sensitive elements 71c to the control board 15 via the cable 15a.

The sensor base 72 is made of a synthetic resin, for example. The sensor base 72 includes, integrally, a support wall portion 72a and a circumferential wall portion 72b vertically provided around the outer circumferential edge of the support wall portion 72a on the rear surface side on the opposite side to the living body. The sensor base 72 supports the pressure sensor portion 71 and the cable 15a connected to the pressure sensor portion 71.

The support wall portion 72a has a rectangular plate-like shape with a predetermined thickness. Here, the wrist 100 side of the support wall portion 72a is the front surface. The support wall portion 72a supports the pressure sensor portion 71 at a main surface 72a1 on the front surface side.

A groove portion 76 is formed at the outer circumferential edge of the main surface 72a1 on the wrist 100 side of the support wall portion 72a, with the support wall portion 72a projecting to the wrist 100 side. The groove portion 76 is formed in a manner allowing the sensor head cover 73 to be engaged with it. The pressure sensor portion 71 is fixed on the main surface 72a1 via the adhesive sheet 71f.

As illustrated in FIG. 15, a plurality of holes (flow holes) 72d are formed in the support wall portion 72a. The plurality of holes 72d extend through the support wall portion 72a in the thickness direction and open to the main surface 72a1 and another main surface 72a2. The plurality of holes 72d are formed in a manner allowing the material of the soft portion 74 to flow through them. The holes 72d communicate with a gap portion 79 described below. The number of holes 72d is four, for example.

Note that in the present embodiment, the pressure sensor portion 71 is fixed to the main surface 72a1 of the support wall portion 72a, and a portion of the pressure sensor portion 71 is disposed opposite the holes 72d. Thus, in the present embodiment, a communication portion 71g that connects the holes 72d and the gap portion 79 is formed at a position where the holes 72d oppose the pressure sensor portion 71. The communication portion 71g is a hole, for example. In the present embodiment, the communication portion 71g includes: a hole 71f1 formed in the adhesive sheet 71f and a hole 71a3 formed in the flexible substrate 71a. Note that the communication portion 71g is not limited to being a hole. For example, it may be a cutout portion. Alternatively, the holes 72d may open to a position of the main surface 72a1 away from the pressure sensor portion 71. In this case, the communication portion 71g is not formed. As such, that the holes 72d communicate with the gap portion 79 includes the holes 72d communicating via the communication portion 71g and the holes 72d communicating directly.

The circumferential wall portion 72b is vertically provided around the outer circumference of the support wall portion 72a on the opposite side to the living body. The circumferential wall portion 72b is fixed to the movable base 64.

The sensor head cover 73 comes into contact with the wrist 100 at an end surface on the wrist 100 side and a portion of the circumferential surface that meets the end surface. The sensor head cover 73 is formed from a synthetic resin material, for example.

The sensor head cover 73 includes, integrally, a protrusion portion 73b and a frame portion 73c vertically provided around the circumferential edge of the protrusion portion 73b on the sensor base 72 side. At least a portion of the opposing surfaces of the sensor head cover 73 and the sensor base 72 are separated from one another, and the gap portion 79 is formed between an inner surface 73g of the sensor head cover 73 and the sensor base 72 and the pressure sensor portion 71.

In the present embodiment, as illustrated in FIGS. 13 and 14, the gap portion 79 is formed between the main surface 72a1 of the support wall portion 72a on which the pressure sensor portion 71 is mounted and the inner surface of the protrusion portion 73b on the pressure sensor portion 71 side, and the gap portion 79 is formed between the outer circumferential surface of the support wall portion 72a and the inner circumferential surface of the frame portion. The gap portion 79 communicates with the plurality of holes 72d.

The protrusion portion 73b has a rectangular plate-like shape, for example. An end surface (flat surface portion) 73d, which is the main surface of the protrusion portion 73b on the living body side, is formed with a flat surface. The protrusion portion 73b includes: the end surface 73d and a circumferential surface 73e formed continuously with the end surface 73d. The circumferential surface 73e follows the thickness direction of the protrusion portion 73b. The end surface 73d and a portion of the circumferential surface 73e correspond to the region of the outer surface of the sensor module 63 that comes into contact with the wrist 100 when the blood pressure measurement device 1 is in use.

An engagement portion 73f that engages with the groove portion 76 of the sensor base 72 is provided at one end of the frame portion 73c on the sensor base 72 side.

The inner surface 73g of the sensor head cover 73 is composed of: the inner surface of the protrusion portion 73b on the pressure sensor portion 71 side; and the inner surface of the frame portion 73c. The gap portion 79 is disposed between the inner surface 73g and the pressure sensor portion 71 and between the inner surface 73g and the sensor base 72. The gap portion 79 are in communication with the plurality of holes 72d.

The sensor head cover 73 with such a configuration is formed from a rubber member in the region that comes into contact with the wrist 100 when the blood pressure measurement device 1 is in use. In the present embodiment, as the end surface 73d of the protrusion portion 73b and a portion of the circumferential surface 73e following the thickness direction correspond to the region that comes into contact with the wrist 100, a portion of the protrusion portion 73b on the wrist 100 side is composed of a rubber portion 75 formed from a rubber material. In other words, a portion of the protrusion portion 73b on the wrist 100 side that forms the outer surface that comes into contact with the wrist 100 is composed of the rubber portion 75 formed from a rubber member. Furthermore, the rubber portion 75 includes the end surface 73d and a portion of the circumferential surface 73e that come into contact with the wrist 100.

A portion of the inner surface 73g is composed of the rubber portion 75. Specifically, an inner surface 75a of the rubber portion 75 on the pressure sensor portion 71 side has an area and a shape opposing all of the pressure sensitive elements 71c of the pressure sensor portion 71 in the thickness direction of the rubber portion 75.

The rubber portion 75 is formed from a rubber material through which pressure from the wrist 100 can transfer to the pressure sensor portion 71 side. An example of the rubber material is a rubber material having frequency characteristics of from 100 Hz to 200 Hz. In the present embodiment, the rubber portion 75 is formed from a rubber material that satisfies these conditions, with silicone rubber as a material.

Portions of the sensor head cover 73 other than the rubber portion 75 are formed from resin, for example. The rubber portion 75 is integrally formed to with the portions other than the rubber portion 75. It is sufficient that the rubber portion 75 is formed from a material that allows the pressure of the radial artery 110 to be detected by the pressure sensor portion 71, and the material of the rubber portion 75 can be selected as appropriate.

The soft portion 74 is provided in the gap portion 79. The soft portion 74 is at least provided between the rubber portion 75 inside the gap portion 79 and the pressure sensitive elements 71c of the pressure sensor portion 71, and the soft portion 74 is configured to allow the pressure from the rubber portion 75 to transfer to the pressure sensitive elements 71c. In other words, the soft portion 74 is configured to allow the pressure of the radial artery 110 transferred from the rubber portion 75 to transfer to the pressure sensitive elements 71c.

In the present embodiment, as illustrated in FIG. 13, the soft portion 74 is disposed in a range from the surface of the rubber portion 75 on the pressure sensor portion 71 side to the adhesive sheet 71f, for example. Note that, as illustrated in FIG. 13, a portion of the sensor head cover 73 is in contact with the adhesive sheet 71f and that, as illustrated in FIG. 14, another portion thereof is not in contact with the adhesive sheet 71f. Therefore, as illustrated in FIG. 14, a portion of the soft portion 74 is located at a position over the adhesive sheet 71f.

Because the soft portion 74 is disposed in a range from the surface of the rubber portion 75 on the pressure sensor portion 71 side to the adhesive sheet 71f, the flexible substrate 71a, the substrate 71b, and all of the pressure sensitive elements 71c of the pressure sensor portion 71 are covered by the soft portion 74, and the soft portion 74 is adhered in the range of the inner surface 73g opposing the pressure sensor portion 71.

As illustrated in FIG. 15, for example, the soft portion 74 is formed by injecting a relatively soft resin material such as a silicone resin into the gap portion 79 via the holes 72d from the main surface 72a2 side. The hardness of the soft portion 74 is less than the hardness of the rubber portion 75. In other words, the hardness of the rubber portion 75 is greater than the hardness of the soft portion 74.

Note that it is sufficient that the soft portion 74 is formed from a material that allows the pressure of the radial artery 110 to be detected by the pressure sensor portion 71, and the thickness, shape that comes into contact with the wrist 100, and material of the soft portion 74 can be selected as appropriate.

As illustrated in FIG. 17, the adjustment portion 53 is configured to adjust the position of the sensor unit 52, with respect to the case 51, in the circumferential direction of the wrist 100. The adjustment portion 53 is located on the outer surface of the case 51 and includes an adjustment catch 53a, the portion of which is fixed to the fixing portion 61b of the movable case 61 via the third hole portion 51e. Also, the adjustment portion 53 includes: graduations 53b provided adjacent to the third hole portion 51e of the case 51 and an instruction portion 53c provided on the adjustment catch 53a that indicates the graduations 53b.

The adjustment catch 53a is connected to the sensor unit 52 by being fixed to the movable case 61. The adjustment catch 53a is configured to move the sensor unit 52. In other words, the adjustment portion 53 is an adjustment mechanism that, by the adjustment catch 53a being moved in the longitudinal direction of the third hole portion 51e, moves the sensor unit 52 along the second groove 51f2 and adjusts the position of the sensor unit 52 with respect to the case 51.

The graduations 53b and the instruction portion 53c are display portions that display the position of the adjustment catch 53a, i.e., the position of the sensor unit 52 connected to the adjustment catch 53a, in a visually recognizable manner.

The fastener 43 includes, for example, one or a plurality of band-like bands and a fixing member such as a hook-and-loop fastener that secures the band wrapped around the wrist 100. The fastener 43 fixes the attach portion 41 and the sensing body 42 to the wrist 100. Note that the fastener 43 may be composed of: a first belt referred to as a parent that includes a buckle; and a second belt referred to as a pointed end that is fixed to the buckle. Also, the fastener 43 may further have a configuration in which the case 51 is fixed to the attach portion 41 by the fastener 43 being wrapped around the case 51.

In other words, the fastener 43 is configured to prevent the case 51 from moving in a direction away from the attach portion 41 when the reaction force, when the sensor module 63 presses against the wrist 100 due to the expansion of the air bag 62, acts on the movable case 61 and when the case 51 is directly pressed by the movable case 61 or indirectly pressed via the adjustment catch 53a from the movable case 61.

Next, an example of a method for manufacturing the sensor module 63 will be described using FIG. 18. FIG. 18 is a flowchart illustrating an example of a method for manufacturing the sensor module 63. The method for manufacturing the sensor module 63 includes: a sensor setting step of setting the pressure sensor portion 71 on the sensor base 72 (step ST11), a cover attaching step of attaching the sensor head cover 73 to the sensor base 72 (step ST12), and a filling step of supplying the material that forms the soft portion 74 (step ST13).

First, in the sensor setting step (step ST11), the plurality of pressure sensitive elements 71c are mounted on the substrate 71b. Next, the substrate 71b on which the plurality of pressure sensitive elements 71c are mounted is mounted on the flexible substrate 71a. In this way, the pressure sensor portion 71 is completed. Next, the pressure sensor portion 71 is fixed on the sensor base 72 via the adhesive sheet 71f.

Then, in the cover attaching step (step ST12), the sensor head cover 73 is put on the sensor base 72. Here, the gap portion 79 is formed between the sensor base 72 and the sensor head cover 73.

Next, the filling step (step ST13) is performed. In the filling step, the integral body of the sensor base 72 and the sensor head cover 73 in an assembled state is orientated so that the protrusion portion 73b faces down in the direction of gravity. In this state, a nozzle 82 through which soft resin flows is inserted into the holes 72d from the main surface 72a2 side, and a predetermined amount of the material of the soft portion 74 is supplied via the holes 72d. The material flows into the gap portion 79 from the holes 72d due to gravity and fills up a portion inside the gap portion 79. In this embodiment, as described above, this portion is the range from the surface of the protrusion portion 73b on the pressure sensor portion 71 side to the adhesive sheet 71f.

The material of the soft portion 74 supplied into the gap portion 79 forms the soft portion 74. Note that, depending on the type of material of the soft portion 74, the soft portion 74 may be formed by cooling or heating. In this manner, the sensor module 63 is completed.

Next, an example of measurement of a blood pressure value using the blood pressure measurement device 1 will be described using FIGS. 19 to 22. FIG. 19 is a flowchart illustrating an example of blood pressure measurement using the blood pressure measurement device 1, illustrating both the operation of the user and the operation of the control unit 33. FIGS. 20 to 22 are explanatory diagrams illustrating an example of blood pressure measurement using the blood pressure measurement device 1.

First, the user searches by palpating the wrist 100 for the position of the radial artery 110 (step ST21). For example, at this time, a visible line may be drawn on the skin above the radial artery 110 with a pen.

The user then separates the sensing body 42 of the sensor device 5 from the attach portion 41. In the present embodiment, the user operates the engagement portion 51b to release the engagement of the case 51 with the base portion 41a and rotates the sensing body 42 about the rotation shaft 51a in a direction away from the attach portion 41.

The user then attaches the device body 4 and the sensor device 5 as illustrated in FIG. 20 (step ST22). As a specific example, the user first passes the wrist 100 through the body fastener 16 of the device body 4 and the fastener 43 of the sensor device 5 and places the device body 4 and the sensor device 5 at a predetermined position on the wrist 100. Next, the body fastener 16 of the device body 4 is tightened, and the device body 4 is fixed to the wrist 100. Here, in a case of configuration in which a cuff is provided on the body fastener 16 of the device body 4, a check is performed to see whether the skin of the wrist 100 is caught in the body fastener 16 (cuff) and whether the body fastener 16 (cuff) is too loose is performed. Next, the position of the sensor device 5 is adjusted so that the opening portion 41b of the attach portion 41 of the sensor device 5 is located at the radial artery 110 of the wrist 100. In addition, the user tightens the fastener 43 of the sensor device 5, and the sensor device 5 is fixed to the wrist 100, with the radial artery 110 held at the position of the opening portion 41b.

Next, as illustrated in FIG. 21, the user palpates the wrist 100 from the opening portion 41b of the attach portion 41 (step ST23) and checks again that the radial artery 110 is located at the opening portion 41b. Then, as illustrated in FIG. 22, the user rotates the sensing body 42 in a direction toward the attach portion 41 and fixes the sensing body 42 to the attach portion 41 via the engagement portion 51b. Note that when the position of the sensing body 42 is misaligned with the radial artery 110, the adjustment catch 53a is operated to adjust the position of the sensing body 42.

Next, the user operates the operation portion 12 to send an instruction to measure the blood pressure. The control unit 33 measures the blood pressure on the basis of the blood pressure measurement instruction (step ST24). At this time, the control unit 33 drives and controls the pump 14, and as illustrated in FIGS. 7 to 12, the air bag 62 is expanded, moving the sensor module 63 progressively toward the wrist 100 from a state of being housed inside the movable case 61, and the sensor head cover 73 and the soft portion 74 of the sensor module 63 are pressed against the region where the radial artery 110 of the wrist 100 is found. By pressing the sensor head cover 73 and the soft portion 74 against this region of the wrist 100, the radial artery 110 is pressed with an appropriate amount of pressure so that a portion of the radial artery 110 is flattened. In this state, the pressure sensitive elements 71c of the pressure sensor portion 71 measure the pressure pulse waves.

Note that the control unit 33 obtains the blood pressure via the tonometry method from the pressure pulse waves of the radial artery 110 detected by the pressure sensor portion 71. Note that prior to blood pressure measurement, the control unit 33 may perform a blood pressure measurement for calibration on the basis of program data stored in the storage unit 32 or may perform a check to determine whether or not the worn state of the device body 4 and/or the sensor device 5 and the position of the pressure sensor portion 71 are correct.

In the blood pressure measurement device 1 with such a configuration, the sensor head cover 73 includes the rubber portion 75 that forms the region that comes into contact with the wrist 100 on the outer surface. Thus, when the blood pressure measurement device 1 is in use, the end surface 73d of the rubber portion 75 and a portion of the circumferential surface 73e along the thickness direction come into contact with the wrist 100. However, because the rubber portion 75 is formed from a rubber member, the protection strength of the surface of the sensor module 63 that comes into contact with the wrist 100 can be improved and damage can be prevented. In addition, the feel felt by the user can be improved.

Additionally, the attach portion 41 is provided with the large opening portion 41b through which palpation is possible, and, because the wrist 100 can be palpated with the sensor device 5 worn in this state, whether or not the sensor device 5 is worn at the predetermined position can be easily determined. In other words, the wrist 100 can be palpated from the opening portion 41b, and, when the sensor device 5 of the blood pressure measurement device 1 is worn on the wrist 100, the sensor device 5 is worn in an ad-lib state on the wrist 100 and the radial artery 110 is found by palpation; thereafter, the sensor device 5 is adjusted in position and worn properly. As a result, the blood pressure measurement device 1 can be easily worn at the appropriate position. In addition, because the sensor device 5 has a configuration that includes the adjustment portion 53, the adjustment catch 53a can be operated even after the sensor device 5 is worn properly on the wrist 100. This allows the position of the sensor unit 52 with respect to the radial artery 110 to be adjusted, which further allows the pressure of the radial artery 110 to be measured at a suitable position.

Furthermore, the sensor device 5 has a configuration in which the sensing body 42 is configured to be moved in a direction away from the attach portion 41 and in which the sensing body 42 rotates away from the attach portion 41 about an axis. Thus, when the sensing body 42 is moved, the sensor module 63 provided on the sensing body 42 moves in a direction away from the opening portion 41b of the attach portion 41.

This can prevent the sensor module 63 from moving while in contact with the wrist 100 and the attach portion 41 when the sensing body 42 is moved with respect to the attach portion 41. Specifically, the sensor unit 52 measures the blood pressure, with the sensor head cover 73 and the soft portion 74 of the sensor module 63 projecting from the opening of the movable case 61, at a position where the wrist 100 can be appropriately pressed via the air bag 62.

Even when the sensing body 42 is moved with respect to the attach portion 41 in this state, in the sensing body 42, the sensor module 63 moves in a direction away from the wrist 100. Thus, the sensing body 42 cannot move in a state of the end surface of the sensor head cover 73 and the soft portion 74 being in contact with the wrist 100 or the attach portion 41. As a result, when the sensing body 42 is moved, damage caused by the sensor module 63 interfering other configurations or the wrist 100 and a load on the wrist 100 can be prevented.

In this way, because the sensor device 5 is provided with the opening portion 41b with a shape that allows palpation through the attach portion 41 and the sensing body 42 is configured to move in a direction away from the attach portion 41 and the wrist 100, damage to the sensor module 63 can be prevented and safety can be improved.

Furthermore, the sensor device 5 has a configuration in which the sensing body 42 is rotated about an axis with respect to the attach portion 41. Thus, a simple configuration can be achieved, with the attachment portion 41c provided on the attach portion 41 and with the rotation shaft 51a journaled in the attachment portion 41c provided on the sensing body 42. Thus, compared to a configuration in which the sensor device 5 is slid in a direction with respect to the attach portion 41, a simpler configuration which is cheaper to manufacture can be achieved.

Also, the sensor device 5 has a configuration in which the sensing body 42 rotates with respect to the attach portion 41 at one end side in the longitudinal direction of the attach portion 41. Thus, substantially the entire region of the upper surface of the attach portion 41 can be exposed to the outside. As a result, the opening portion 41b of the attach portion 41 is completely exposed, allowing the size of the shape of the opening portion 41b required for palpation to be kept as small as possible. Furthermore, because a rail configuration for sliding the sensing body 42 with respect to the attach portion 41 or a configuration for supporting the sensing body 42 on the attach portion 41 after sliding are not necessary, the shape in the width direction of the wrist 100 of the sensor device 5 can be kept as small as possible. This allows the sensor device 5 to be made compact.

As described above, according to the blood pressure measurement device 1 of an embodiment of the present invention, the sensor head cover 73 includes the rubber portion 75 that forms the region that comes into contact with the wrist 100 on the outer surface. Thus, the protection strength of the surface of the sensor module 63 that comes into contact with the wrist 100 can be improved and damage can be prevented.

Note that the present invention is not limited to the embodiment described above. For example, in another embodiment illustrated in FIG. 23, the rubber portion 75 may constitute the inner surface 75a of the sensor head cover 73 on the pressure sensor portion 71 side, and a first protrusion portion 77a projecting toward the pressure sensor portion 71 may be formed on at least a portion of the region opposite the plurality of pressure sensitive elements 71c of the inner surface 75a of the rubber portion 75 on the pressure sensor portion 71 side. Here, the region of the inner surface 75a opposite the plurality of pressure sensitive elements 71c corresponds to the region opposite in the thickness direction of the rubber portion 75.

In this embodiment, the first protrusion portion 77a is formed at a position, opposite a central region of the end surface 73d, of the inner surface 75a, for example. The first protrusion portion 77a projects in a manner so that it does not come into contact with the pressure sensitive elements 71c. By disposing a hard portion, i.e., the first protrusion portion 77a, at a position near the pressure sensitive elements 71c, compared to disposing the soft portion 74, the pressure of the radial artery 110 is more efficiently transferred to the pressure sensitive elements 71c.

As described above, in another embodiment with a configuration including the first protrusion portion 77a, as illustrated in FIGS. 24 and 25, the first protrusion portion 77a extends in the longitudinal direction of the pressure sensitive element array 71d and has a tapered shape that progressively decreases in cross-sectional area toward the pressure sensitive element array 71d.

FIG. 24 illustrates the sensor module 63 in a state of taken along a cross-section in the longitudinal direction of the pressure sensitive element array 71d. FIG. 25 is a cross-sectional view taken along a cross-section line Fkσ-Fkσ illustrated in FIG. 24 and illustrates the sensor module 63 in a state of taken along a cross-section orthogonal to the longitudinal direction of the pressure sensitive element array 71d.

With this configuration, as illustrated in FIG. 24, the first protrusion portion 77a, for example, is formed in a shape extending from a position opposite one end in the longitudinal direction of the pressure sensitive element array 71d to a position opposite the other end.

Furthermore, as illustrated in FIG. 25, the first protrusion portion 77a is formed in a tapered shape with a cross-section that decreases toward the pressure sensitive element array 71d, such as a shape with a triangular cross-section. Note that in the present embodiment and the modified example, two pressure sensitive element arrays 71d are provided. As described above, in an example in which the plurality of pressure sensitive element arrays 71d are provided, the first protrusion portion 77a is formed in a shape that tapers toward the center of the plurality of pressure sensitive element arrays 71*d* in the direction in which the plurality of pressure sensitive element arrays 71*d* are arranged side by side. In other words, in an example in which two pressure sensitive element arrays 71*d* are provided, the first protrusion portion 77*a* is formed in a shape that tapers toward a point between the two pressure sensitive element arrays 71*d*. In an example in which three pressure sensitive element arrays 71*d* are provided, the first protrusion portion 77*a* is formed in a shape that tapers toward one pressure sensitive element array 71*d* disposed in the center. In an example in which one pressure sensitive element array 71*d* is provided, the first protrusion portion 77*a* is formed in a shape that tapers toward the one pressure sensitive element array 71*d*.

In an example in which the cross-section of the first protrusion portion 77*a* is formed in a triangular shape, both side surfaces 77*a*1 of the first protrusion portion 77*a* are formed as flat surfaces inclined with respect to the projection direction of the first protrusion portion 77*a*. Note that in another example in which the first protrusion portion 77*a* is formed in a tapered shape with a cross-section that decreases toward the pressure sensitive element array 71*d*, the shape may have a cross-section along a direction toward the pressure sensitive element array 71*d* that is a trapezoidal shape or a semi-circular shape.

In this manner, the first protrusion portion 77*a* is formed in an elongated shape in the longitudinal direction of the pressure sensitive element array 71*d*, i.e., the direction in which the plurality of pressure sensitive elements 71*c* are arranged side by side, and is formed in shape with a cross-sectional shape that progressively tapers toward the center of the plurality of pressure sensitive element arrays 71*d* in the direction in which the pressure sensitive element arrays 71*d* are arranged side by side. This allows the pressure from the wrist 100 to efficiently transfer to the pressure sensitive element array 71*d*.

Note that the first protrusion portion 77*a* illustrated in FIGS. 24 and 25 have a tapered shape progressively tapering toward the center of the plurality of pressure sensitive element arrays 71*d* in the direction in which the plurality of pressure sensitive element arrays 71*d* are arranged side by side and have a shape that extends in the direction in which the plurality of pressure sensitive elements 71*c* are arranged side by side. However, only one may be the case. In other words, the cross-sectional area may have: a shape that extends in the direction in which the plurality of pressure sensitive elements 71*c* are arranged side by side; or a shape that progressively tapers toward, in the case in which the plurality of pressure sensitive element arrays 71*d* are provided, the center of the plurality of pressure sensitive element arrays 71*d* in the direction in which the plurality of pressure sensitive element arrays 71*d* are arranged side by side or tapers toward, in the case in which one pressure sensitive element array 71*d* is provided, the one pressure sensitive element array 71*d*.

Furthermore, in another embodiment illustrated in FIG. 26, in addition to the first protrusion portion 77*a*, a second protrusion portion 77*b* that projects toward the wrist 100 is formed on the end surface 73*d*. The second protrusion portion 77*b* is formed with a smooth surface because it comes into contact with the wrist 100.

In the present embodiment, the second protrusion portion 77*b* is formed centrally on the end surface 73*d* in a dome shape. However, the shape of the second protrusion portion 77*b* is not limited to a dome shape. In other examples, it may be hemispherical, for example. Additionally, the second protrusion portion 77*b* is not limited to being centrally disposed on the end surface 73*d*. The second protrusion portion 77*b* may be formed in at least one portion of the region of the end surface 73*d* opposite the plurality of pressure sensitive elements 71*c* of the pressure sensor portion 71. Here, the region of the end surface 73*d* opposite the plurality of pressure sensitive elements 71*c* of the pressure sensor portion 71 corresponds to the region opposite the rubber portion 75 in the thickness direction.

Note that in FIG. 26, a configuration in which the rubber portion 75 includes the first protrusion portion 77*a* and the second protrusion portion 77*b* is illustrated. However, no such limitation is intended. In other examples, the rubber portion 75 may not include the first protrusion portion 77*a* and include the second protrusion portion 77*b*.

Alternatively, in the embodiment illustrated in FIG. 27, the entire sensor head cover 73 is formed from the same material as the rubber portion 75. Also, in a case of a configuration in which the sensor head cover 73 is formed from the same material as the rubber portion 75 in this manner, as illustrated in FIGS. 23 to 25, at least one of the first protrusion portion 77*a* or the second protrusion portion 77*b* may be formed.

Alternatively, in another embodiment illustrated in FIG. 28, an opening 73*a* is provided in the region of the rubber portion 75 that comes into contact with the wrist 100, and the opening 73*a* is closed off by a first portion 78*a* and a second portion 78*b*. The opening 73*a* is formed in a region opposite all of the pressure sensitive elements 71*c* of the pressure sensor portion 71. Here, a region opposite all of the pressure sensitive elements 71*c* corresponds to the region opposite in the thickness direction of the rubber portion 75.

The first portion 78*a* is located on the inner side of the opening 73*a* and is formed from the same material as the rubber portion 75. The first portion 78*a* has a disk-like shape, for example.

The second portion 78*b* is located between the first portion 78*a* and the inner circumferential surface of the opening 73*a* and has an annular shape that closes off the space between the first portion 78*a* and the inner circumferential surface of the opening 73*a*. The second portion 78*b* is formed from the same material as the soft portion 74. Note that the second portion 78*b* may be formed integrally with the soft portion 74.

In a configuration including the first portion 78*a* and the second portion 78*b* such as this, as illustrated in FIG. 15, a smooth surface 81*a* of an opposing to plate 81 is brought into contact with the end surface 73*d* in a state of the first portion 78*a* being disposed in the opening 73*a*, and then the opening 73*a* is closed off. Note that the opposing plate 81 is illustrated by the two-dot dash line. With the opening 73*a* closed off by the smooth surface 81*a* of the opposing plate 81, the material of the soft portion 74 is injected into the holes 72*d* via the nozzle 82. The injected material forms the soft portion 74 and the second portion 78*b*. Furthermore, the first portion 78*a* is bonded to the soft portion 74 and the second portion 78*b*, fixing the first portion 78*a* in the opening 73*a*.

Alternatively, the second portion 78*b* may be a separate member from the soft portion 74. In this case, the second portion 78*b* formed in an annular shape, for example, is formed by being disposed in the opening 73*a*.

In this embodiment, the periphery of the first portion 78*a* that forms the central portion of the opening 73*a* of the rubber portion 75 is surrounded by the second portion 78*b* formed from the same material as the soft portion 74. According to this configuration, the first portion 78*a* is supported by the second portion 78*b*, which has a lower hardness than the first portion 78*a*. This allows the first portion 78a to easily move toward the pressure sensor portion 71 side. Thus, the pressure change of the wrist 100 is more easily transmitted to the pressure sensor portion 71.

In another embodiment with a configuration in which the opening 73a is formed in the sensor head cover 73 and the first portion 78a and the second portion 78b are disposed in the opening 73a in this manner, as illustrated in FIG. 29, the first portion 78a may include the first protrusion portion 77a and the second protrusion portion 77b. As illustrated in FIGS. 26 and 27, the first protrusion portion 77a has a shape with a cross-sectional area that progressively decreases toward the pressure sensitive element array 71d, and the first protrusion portion 77a extends in a direction in which the plurality of pressure sensitive elements 71c are arranged side by side, i.e., the longitudinal direction of the pressure sensitive element array 71d. Note that the configuration is not limited to including both the first protrusion portion 77a and the second protrusion portion 77b, and the configuration may include only one thereof.

Also, in another example of an embodiment in which the rubber portion 75 includes the opening 73a, the first portion 78a may be not provided, and the opening 73a may be closed off by the second portion 78b. In this example, the second portion 78b may be integrally formed with the soft portion 74 from the material of the soft portion 74 injected from the holes 72d, for example.

In this embodiment, the end surface of the second portion 78b on the wrist 100 side, i.e., the end surface 73d of the sensor head cover 73, may be flat. Alternatively, as illustrated in FIG. 30 as a modified example, a protrusion portion 78b1 projecting toward the wrist 100 side may be formed on the end surface of the second portion 78b on the wrist 100 side. By forming a recess corresponding to the protrusion portion 78b1 in the smooth surface 81a of the opposing plate 81 illustrated in FIG. 15, the protrusion portion 78b1 can be formed by this recess.

In the example described above, at least the region of the sensor head cover 73 that comes into contact with the wrist 100 is formed from the rubber portion 75, and the remaining portions are formed from a resin material. In yet another embodiment illustrated in FIG. 31, the sensor head cover 73 is formed from a material that is not the rubber portion 75, an opening 73m is formed in the region opposite the pressure sensor portion 71, and the rubber portion 75 is configured by a separate member from the sensor head cover 73 being fixed on the sensor head cover 73.

The rubber portion 75 is provided in a region opposite the wrist 100, with the sensor head cover 73 not coming into contact with the wrist when the blood pressure measurement device 1 is in use. Also in this embodiment, because the rubber portion 75 comes into contact with the wrist 100, the protection strength of the surface of the sensor module 63 that comes into contact with the wrist 100 can be improved and damage can be prevented.

Furthermore, in this embodiment, the sensor head cover 73 formed from resin has been used in known configurations can be used. In other words, it is only necessary to fix the rubber portion 75 to the sensor head cover 73.

Note that in the embodiment illustrated in FIG. 31, the rubber portion 75 includes the opening 73a that communicates with the opening 73m of the sensor head cover 73. The opening 73m and the opening 73a are closed off by the soft portion 74. Thus, a portion of the end surface 73d is formed from the soft portion 74. However, in another modified example, the rubber portion 75 may have a configuration not including the opening 73a. In other words, the rubber portion 75 may have a shape that does not close off the opening 73m.

The present invention is not limited to the embodiments described above. In the example described above, the blood pressure measurement device 1 has a configuration in which the device body 4 and the sensor device 5 are different bodies. However, no such limitation is intended. For example, as illustrated in FIGS. 32 and 33, the blood pressure measurement device 1 may have a configuration in which the device body 4 and the sensor device 5 are integrally formed. The blood pressure measurement device 1 with such a configuration, for example, may have configuration in which the operation portion 12, the display portion 13, the pump 14, and the control board 15 used in the device body 4 are provided in the case 51 of the sensing body 42.

Also, in the example described above, the blood pressure measurement device 1 has a configuration in which the sensing body 42 moves in a direction away and a direction toward the attach portion 41 by the sensing body 42 rotating with respect to the attach portion 41 about an axis. However, no such limitation is intended. For example, as illustrated in FIG. 34, the blood pressure measurement device 1 may have a configuration in which the sensing body 42 moves in a direction away and a direction toward the attach portion 41 by the attach portion 41 and the sensing body 42 being separated. In the case in which the blood pressure measurement device 1 has this configuration, the engagement portions 51b are provided at a plurality of positions on the case 51 of the sensing body 42, and the sensing body 42 engages with the attach portion 41 at these positions.

Also, in the examples described above, the blood pressure measurement device 1 has a configuration that measures the pressure of the radial artery 110 and that obtains the blood pressure by the tonometry method. However, no such limitation is intended. In another example, the pressure of the ulnar artery 112 is measured. The blood pressure measurement device 1 may also have a configuration in which the blood pressure is obtains via a method other than the tonometry method. In other words, as long as the blood pressure measurement device 1 has a configuration in which the sensor module 63 that comes into contact with the wrist 100 is configured to move with respect to the opening portion 41b of the attach portion 41 and the wrist 100 and in which the sensing body 42 moves while in contact with and the wrist 100 or in other configurations, another blood pressure measurement method may be used.

In the examples described above, the opening portion 41b of the attach portion 41 allows for palpation. However, no such limitation is intended. The opening portion 41b may be an opening that does not allow palpation.

In other words, the embodiments described above are merely examples of the present invention in all respects. Of course, various modifications and variations can be made without departing from the scope of the present invention. Thus, specific configurations in accordance with an embodiment may be adopted as appropriate at the time of carrying out the present invention.

REFERENCE SIGNS LIST

1 Blood pressure measurement device
4 Device body
5 Sensor device
11 Body case
12 Operation portion 13 Display portion
14 Pump
14a Tube
15 Control board
15a Cable
16 Body fastener
21 Button
31 Communication unit
32 Storage unit
33 Control unit
41 Attach portion
41a Base portion
41b Opening portion
41c Attachment portion
42 Sensing body
43 Fastener
51 Case
51a Rotation shaft
51b Engagement portion
51c First hole portion
51d Second hole portion
51e Third hole portion
51f Guide groove
51f1 First groove
51f2 Second groove
52 Sensor unit
53 Adjustment portion
53b Graduations
53c Instruction portion
61 Movable case
61a Guide projection
61b Fixing portion
62 Air bag
63 Sensor module
71 Pressure sensor portion
71a Flexible substrate
71b Substrate
71c Pressure sensitive element
71d Pressure sensitive element array
72 Sensor base
72a Support wall portion
73 Sensor head cover
73a Opening
73b Protrusion portion
73c Frame portion
73d End surface
73e Circumferential surface
73g Inner surface
74 Soft portion
75 Rubber portion
76 Groove portion
78a First portion
78b Second portion
79 Gap portion
100 Wrist
110 Radial artery
111 Radius
112 Ulnar artery
113 Ulna
114 Tendon

The invention claimed is:

1. A sensor module, comprising:
a sensor base;
a pressure sensor portion fixed to the sensor base;
a sensor head cover fixed to the sensor base, the sensor head cover
including a rubber portion that forms, on an outer surface, at least a region that comes into contact with a living body and that allows pressure from the living body to transfer to a side of the pressure sensor portion,
including a protrusion portion projecting toward the living body, an end surface thereof being formed with a flat surface, and at least a portion of the protrusion portion being formed from the rubber portion, and
forming a gap portion between an inner surface, at least a portion of the inner surface being composed of the rubber portion, and the sensor base and the pressure sensor portion; and
a soft portion disposed in the gap portion at least between the rubber portion and the pressure sensor portion, the soft portion
having a lower hardness than the rubber portion and
allowing pressure from the rubber portion to transfer to the pressure sensor portion, wherein
the sensor head cover includes:
an opening portion formed in a region, opposite the pressure sensor portion, of the sensor base;
a first portion located in the opening portion and formed from an identical material to the rubber portion; and
a second portion located on an outer side of the first portion in the opening portion and formed from an identical material to the soft portion, the second portion closing off space between an edge of the opening portion and the first portion.

2. The sensor module according to claim 1, wherein
the pressure sensor portion includes a pressure sensitive element; and
a first protrusion portion projecting toward the pressure sensitive element is provided in at least a portion of a region, opposite the pressure sensitive element, of an inner surface of the rubber portion on a side of the pressure sensor portion.

3. The sensor module according to claim 2, wherein
the first protrusion portion is configured to have a tapered shape with a cross-sectional area that progressively decreases toward a side of the pressure sensitive element.

4. The sensor module according to claim 2, wherein the pressure sensor portion includes a pressure sensitive element array including a plurality of the pressure sensitive elements configured to be arranged side by side; and the first protrusion portion is configured to have a shape that extends in a direction in which the plurality of pressure sensitive elements are arranged side by side.

5. The sensor module according to claim 1, wherein
a second protrusion portion projecting toward the living body is provided in at least a portion of a region, opposite the pressure sensor portion, of an outer surface of the rubber portion.

6. The sensor module according to claim 1, wherein
the pressure sensor portion includes a pressure sensitive element; and
a first protrusion portion projecting toward the pressure sensitive element is provided in at least a portion of a region, opposite the pressure sensitive element, of an inner surface of the first portion on a side of the pressure sensor portion.

7. The sensor module according to claim 6, wherein
the first protrusion portion is configured to have a tapered shape with a cross-sectional area that progressively decreases toward a side of the pressure sensitive element.

8. The sensor module according to claim 6, wherein the pressure sensor portion includes a pressure sensitive element array including a plurality of the pressure sensitive elements configured to be arranged side by side; and the first protrusion portion is configured to have a shape that extends in a direction in which the plurality of pressure sensitive elements are arranged side by side.

9. The sensor module according to claim 1, wherein
the first portion includes a second protrusion portion projecting toward the living body.

10. A blood pressure measurement device comprising:
a sensor module including:
  a sensor base;
  a pressure sensor portion fixed to the sensor base;
  a sensor head cover fixed to the sensor base, the sensor head cover
    including a rubber portion that forms, on an outer surface, at least a region that comes into contact with a living body and that allows pressure from the living body to transfer to a side of the pressure sensor portion,
    including a protrusion portion projecting toward the living body, an end surface thereof being formed with a flat surface, and at least a portion of the protrusion portion being formed from the rubber portion, and
    forming a gap portion between an inner surface, at least a portion of the inner surface being composed of the rubber portion, and the sensor base and the pressure sensor portion; and
  a soft portion disposed in the gap portion at least between the rubber portion and the pressure sensor portion, the soft portion
    having a lower hardness than the rubber portion and allowing pressure from the rubber portion to transfer to the pressure sensor portion;
an attach portion including:
  an opening portion provided at a position opposite the living body, the sensor module being disposed in the opening portion, and
  an end surface that curves conforming to a shape in the circumferential direction of a portion of the living body;
a fastener provided on the attach portion; and
a case provided on the attach portion, the case housing the sensor module, wherein
the sensor head cover includes:
an opening portion formed in a region, opposite the pressure sensor portion, of the sensor base;
a first portion located in the opening portion of the sensor head cover and formed from an identical material to the rubber portion; and
a second portion located on an outer side of the first portion in the opening portion and formed from an identical material to the soft portion, the second portion closing off space between an edge of the opening portion and the first portion.

* * * * *